US010881306B2

(12) United States Patent
Grimbert et al.

(10) Patent No.: US 10,881,306 B2
(45) Date of Patent: Jan. 5, 2021

(54) METHOD AND DEVICE FOR MONITORING BLOOD PRESSURE MEASUREMENT BY ARTERIAL CATHETERIZATION OF A PATIENT

(71) Applicants: UNIVERSITE JOSEPH FOURIER—GRENOBLE 1, St. Martin d'Héres (FR); AUTOMATISME ET INFORMATIQUE INDUSTRIELLE, Cran Gevrier (FR)

(72) Inventors: Francis Grimbert, Biviers (FR); Yves Lavault, Cran Gevrier (FR)

(73) Assignees: Universite Joseph Fourier—Grenoble 1, St. Martin d'Heres (FR); Automatisme et Informatique Industrielle, Cran Gevrier (FR)

( * ) Notice: Subject to any disclaimer, the term of this patent is extended or adjusted under 35 U.S.C. 154(b) by 249 days.

(21) Appl. No.: 14/366,512

(22) PCT Filed: Dec. 21, 2012

(86) PCT No.: PCT/EP2012/076582
§ 371 (c)(1),
(2) Date: Jun. 18, 2014

(87) PCT Pub. No.: WO2013/092969
PCT Pub. Date: Jun. 27, 2013

(65) Prior Publication Data
US 2015/0126880 A1 May 7, 2015

(30) Foreign Application Priority Data
Dec. 22, 2011 (FR) .................................. 11 62302

(51) Int. Cl.
*A61B 5/0215* (2006.01)
*A61B 5/00* (2006.01)

(52) U.S. Cl.
CPC .......... *A61B 5/0215* (2013.01); *A61B 5/0004* (2013.01); *A61B 5/6852* (2013.01);
(Continued)

(58) Field of Classification Search
CPC ..... A61B 5/0215; A61B 5/746; A61B 5/0004; A61B 5/6852; A61B 5/7203; A61B 5/743;
(Continued)

(56) References Cited

U.S. PATENT DOCUMENTS 6,290,652 B1 * 9/2001 Wellnhofer .......... A61B 5/7257
600/486
8,926,525 B2 * 1/2015 Hulvershorn ........ A61B 5/0215
600/561
(Continued)

FOREIGN PATENT DOCUMENTS

DE 3927990 A1 * 2/1991 ........... A61B 5/0215
DE 3927990 A1 2/1991

OTHER PUBLICATIONS

Brower, R. W., et al.; "A fully automatic device for compensating for artifacts in conventional catheter-manometer pressure recordings," Biomed Eng, 10, 1975, pp. 305-310.
(Continued)

*Primary Examiner* — Meredith Weare
(74) *Attorney, Agent, or Firm* — Harness, Dickey & Pierce, PLC

(57) ABSTRACT

A method is disclosed for continuously monitoring a blood pressure measurement using a sensor connected by a hydraulic link to an arterial catheter, the method includes determining the dynamic parameters of the link, analyzing
(Continued)

the frequency content of the incident signal, detecting one of the following situations: (a) ability of the link to transmit the incident signal with a distortion below a threshold, (b) ability of the link to transmit the incident signal with a distortion above the threshold and possibility of correcting the measured signal, (c) inability of the link to transmit the incident signal with a distortion below the threshold and impossibility of correcting the measured signal, periodic application of a mechanical action to the tubing providing the hydraulic link.

29 Claims, 12 Drawing Sheets

(52) U.S. Cl.
CPC ............ *A61B 5/7203* (2013.01); *A61B 5/743* (2013.01); *A61B 5/746* (2013.01); *A61B 2560/0266* (2013.01); *A61B 2560/066* (2013.01); *A61B 2562/0247* (2013.01); *A61B 2562/225* (2013.01)

(58) Field of Classification Search
CPC ...... A61B 2560/066; A61B 2562/0247; A61B 2562/225; A61B 2560/0266
See application file for complete search history.

(56) References Cited

U.S. PATENT DOCUMENTS

| | | | |
|---|---|---|---|
| 9,442,036 B2 * | 9/2016 | Furmanski | A61M 1/3653 |
| 2004/0024294 A1 | 2/2004 | Wellnhofer | |
| 2005/0203350 A1 * | 9/2005 | Beck | A61B 5/0002 600/300 |
| 2006/0064021 A1 | 3/2006 | Hefele | |
| 2010/0094113 A1 | 4/2010 | Robinson et al. | |
| 2010/0241013 A1 | 9/2010 | Hatib | |
| 2010/0331708 A1 | 12/2010 | Hatib | |
| 2011/0060229 A1 * | 3/2011 | Hulvershorn | A61B 5/0215 600/486 |
| 2011/0106466 A1 * | 5/2011 | Furmanski | A61M 1/3653 702/51 |
| 2011/0275944 A1 * | 11/2011 | Qasem | A61B 5/022 600/493 |

OTHER PUBLICATIONS

Gardner, Reed M.; "Direct Blood Pressure Measurement—Dynamic Response Requirements," Anesthesiology, 54, 1981, pp. 227-236.

Allan, M. W. B.; "Measurement of Arterial Pressure Using Catheter-Transducer Systems," British Journal of Anaesthesia, 60, 1988, pp. 413-418.

Kleinman, Bruce; "Understanding natural frequency and damping and how they relate to the measurement of blood pressure," J Clin Monit, 5, Apr. 1989, pp. 137-147.

Paulsen, A. William; "Implications for Clinical Monitoring of Intra-Arterial Blood Pressure Based on the Frequency Content of Worst-Case Pressure Waveforms," Medical Instrumentation & Technology, May-Jun. 1993, pp. 217-234.

Kinefuchi, Yoshio, et al.; "Evaluation of dynamic response of catheter-manometer systems for pulmonary arterial pressure," J Appl Physiol, 77 (4), 1994, pp. 2023-2028.

Billiet, E., et al.; "Pressure measurement evaluation and accuracy validation: the Gabarith test," Intensive Care Medicine 24 (12), 1998, pp. 1323-1326.

Promonet, Claude, et al.; "Time-dependent Pressure Distortion in a Catheter-Transducer System," Anesthesiology, 92 (1), Jan. 2000, pp. 208-218.

Kanazawa, Masahiro, et al.; "Relationship between Aortic-to-radial Arterial Pressure Gradient after Cardiopulmonary Bypass and Changes in Arterial Elasticity," Anesthesiology, V. 99, No. 1, Jul. 2003, pp. 48-53.

Ercole, A.; "Attenuation in invasive blood pressure measurement system," British Journal of Anaesthesia, 96 (5), Mar. 27, 2006, pp. 560-562.

Dellinger, R. Phillip, et al.; "Surviving Sepsis Campaign: international guidelines for management of severe sepsis and septic shock: 2008," Critical Care Medicine, Dec. 4, 2007, 36(1), pp. 296-327.

Shimada, Masato et al; "Estimation of Aortic-to-radial Artery Distribution of Arterial Wall Elasticity," Tokai J. Exp. Clin. Med., vol. 33, No. 1, 2008, pp. 1-5.

Mayer, Jochen, et al.; "Continuous Arterial Pressure Waveform-Based Cardiac Output Using the FloTrac/Vigileo: A Review and Meta-analysis," Journal of Cardiothoracic and Vascular Anesthesia, 23 (3), Jun. 2009, pp. 401-406.

Cannesson, Maxime; "Arterial Pressure Variation and Goal-Directed Fluid Therapy," Journal of Cardiothoracic and Vascular Anesthesia, 24 (3), 2010, pp. 487-497.

Hatib, Feras, et al.; "Peripheral vascular decoupling in porcine endotoxic shock," J. Appl. Physiol., 111, 2011, pp. 853-860.

Thiele, Robert H., et al.; "Arterial waveform analysis for the anesthesiologist: past, present, and future concepts," Anesth Analg. vol. 113, No. 4, Oct. 2011, pp. 766-776.

Fok, Henry, et al.; "Regulation of Vascular Tone and Pulse Wave Velocity in Human Muscular Conduit Arteries—Selective Effects of Nitric Oxide Donors to Dilate Muscular Arteries Relative to Resistance Vessels," Hypertension, Nov. 2012, pp. 1220-1225.

* cited by examiner

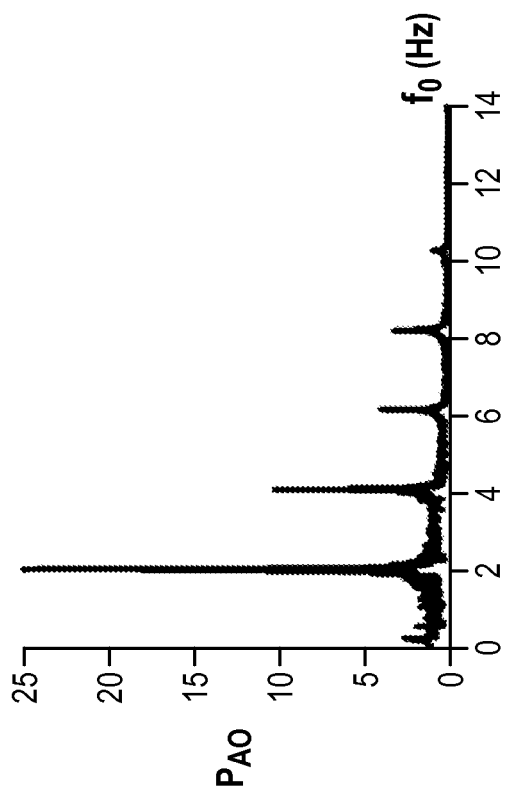
FIG. 13A
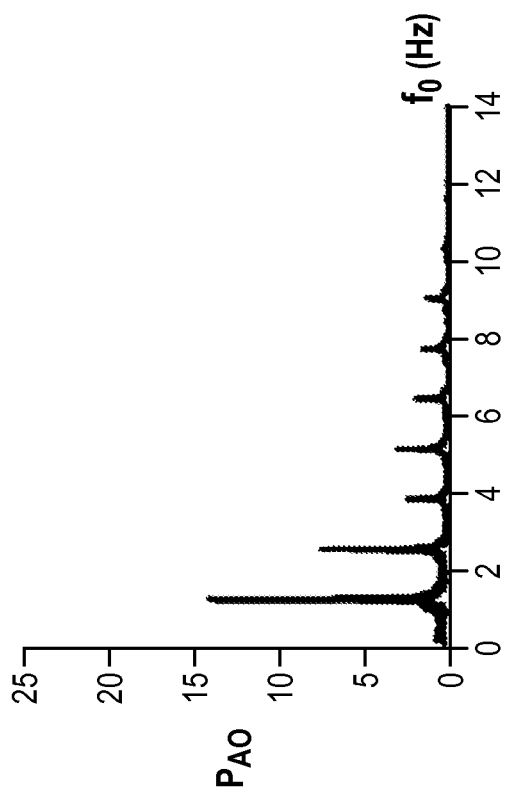
FIG. 13B
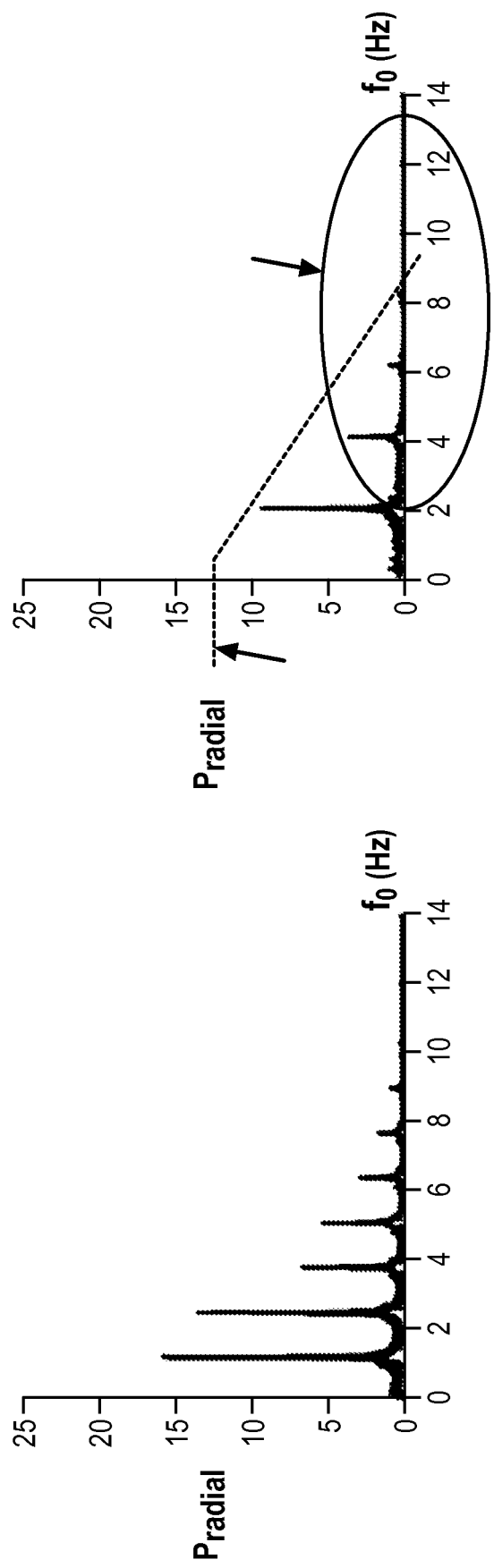

METHOD AND DEVICE FOR MONITORING BLOOD PRESSURE MEASUREMENT BY ARTERIAL CATHETERIZATION OF A PATIENT

CROSS-REFERENCE TO RELATED APPLICATIONS

This application is a National Phase Entry of International Application No. PCT/EP2012/076582, filed on Dec. 21, 2012, which claims priority to French Patent Application Serial No. 1162302, filed on Dec. 22, 2011, both of which are incorporated herein by reference.

FIELD OF THE INVENTION

The present invention relates to a method and a device for monitoring and, where needed, continuous correction of the blood arterial pressure measurement by arterial catheter of a patient.

SUMMARY

Measurements of blood arterial pressure by arterial catheter, especially of the radial artery, of a patient are current practice in intensive care units, in major surgery operating rooms and in interventional cardiology. In fact, this technique allows on the one hand a continuous arterial pressure monitoring which, due to the pathology of the patient, is likely to vary substantially and to a large degree. Also, this technique is compatible with regular sampling of arterial blood for blood gas analysis and blood biological analysis.

FIG. 1 illustrates a device currently widely used for measuring arterial pressure by catheter of the radial artery. This device comprises a catheter 1 introduced into the radial artery of the patient. This catheter has two ends:

the arterial inlet where the hydraulic signal of the arterial pressure of the patient is applied, called an "incident signal".

the external outlet which is connected by tubing 2 to a pressure transducer 3.

The tubing 2 is relatively long so the patient can be moved, for example in view of care, toilet, etc., without moving the pressure transducer 3. So, the tubing 2 typically has a length of around 1.5 metres but can be shorter or longer. The transducer 3 is also connected to a pressurized saline-filled bag 4 via considerable resistance, ensuring slow continuous flush of saline to prevent reflux of blood coming from the catheter, which might cause thrombi to form.

Subject to some possible distortions, the hydraulic connection consisting of the saline-filled tubing 2, which is theoretically incompressible, therefore transmits the arterial pressure of the patient to the transducer 3 which transforms the transmitted signal into an electric signal called a "measured signal". Resistance opposing passage of saline from the bag 4 can be made by action on a pull-tab 5, allowing fast flush of the circuit by a large saline flow. On the other hand, a three-way stopcock is interposed in the tubing 2. Said stopcock 6 draws blood samples by way of a syringe 7.

The pressure transducer 3 also forms part of a measurement chain which will now be described briefly. The pressure transducer 3 is generally of the piezoresistive type and is run in a Wheatstone bridge assembly. The transducer 3 is connected, by means of a cable 8, to a preamplifier module 9 which ensures its feed.

The preamplifier module 9 comprises a galvanic (optoelectronic or other) insulation stage to ensure electrical protection of the patient. The module 9 also comprises a device for protection of electronic components from any overloads caused by use of a defibrillator. It further comprises a low-pass filter whereof the cut-off frequency varies or even can be regulated between 5 Hz and 40 Hz. Finally, the preamplifier module 9 ensures digitising of the measured arterial pressure signal so it can be run by a monitor 10 placed at the bedside of the patient.

The bedside monitor 10 displays the digitised signal in the form of an arterial pressure curve and transmits it to a central system where it is recorded. It also displays the systolic, diastolic and mean values of this arterial pressure curve and transmits them to a central system where they are recorded. Due to the sterility constraints of these invasive measures, the transducer 3 is generally disposable and supplied in a sterile packaging with the tubing 2.

The advantages of this type of device are the following. On the one hand, it takes a continuous measurement of the arterial pressure, as opposed to sphygmomanometry and oscillometry. This is of major interest for monitoring patients with hemodynamic instability. Also, continuous follow-up of systolic arterial pressure (and not only of mean arterial pressure) proves to be particularly interesting information in three fields which use derived indices of systolic arterial pressure.

A first example is that of evaluation of the intravascular volume of a patient under mechanical ventilation. In fact, mechanical ventilation creates a variation in right and left ventricular preloads, cardiac output and the difference between systolic arterial pressure and diastolic arterial pressure. The index designated by APP is defined during a single respiratory cycle as being the ratio between, on the one hand, the difference between the maximum distance and the minimum distance between systolic pulse pressure and diastolic pulse pressure, and on the other hand, the mean maximum and minimum of the pulse pressure [1].

A second example of derived index is that of the arterial pulse contour based cardiac output measurement [2]. A third example of derived index is that of evaluation of cardiac ventricular contractility, for which the maximum arterial pressure change ($dP/dt_{max}$) in the arteries is measured [3].

Another advantage to this device is that it makes it easy to take many blood and gas samples of the arterial blood, as the catheter is installed permanently in the artery of the patient. Also, the measuring method is robust, that is, it is minimally sensitive to the patient being shifted frequently, contrary to applanation arterial tonometry and finger photoplethysmography. Finally, the cost of the device is low to buy and service (the transducer and the tubing are supplied sterile and disposable).

Despite these advantages, this measuring method suffers from a number of disadvantages or limitations. On the one hand, the hydraulic connection between the catheter and the transducer is likely to generate distortions of the measured signal by the transducer. Many scientific and technical publications ascertain the frequency and cause of such distortions [4] [5]. In fact, the hydraulic connection, comprising tubing exhibiting some compliance and containing a column of saline, behaves like a mechanical mass/spring system.

This system is governed by a differential equation of the second order and can be characterized by a transfer function H(p) of the type:

$$H(p) = \frac{1}{\frac{p^2}{\omega_0^2} + \frac{2z}{\omega_0}p + 1}$$

where p is a Laplace variable, z is the damping factor and $\omega_0$ is the natural pulsation, expressed in rad/s and equal to $2\pi f_0$, where $f_0$ is the natural frequency, expressed in Hz.

According to the values of the parameters of this transfer function ($f_0$ and z), more or less significant distortions can occur between, on the one hand the incident signal applied to the arterial inlet of the catheter corresponding to the arterial pressure of the patient (at the input of the system), as a function of its spectral content, and on the other hand the signal measured by the transducer (at the output of the system). The most notable distortions can reach 20% of the systolic arterial pressure. These distortions comprise on the one hand overestimation of the systolic arterial pressure, and on the other hand underestimation of the diastolic arterial pressure, which appear more frequently on signals having a rapidly rising edge transmitted by resonant tubing having a low damping coefficient.

By way of a reference plotting measured by a pressure transducer located at the arterial inlet of the catheter (curve (a)) and a plotting measured by a pressure transducer placed conventionally at a distance of around 1.5 m from the catheter (curve (b)), FIG. 2 shows overestimation ∂ of the systolic arterial pressure of the order of 15% by the remote transducer. Also, it has been shown that the parameters ($f_0$, z) of the transfer function could evolve significantly over time, probably due to the presence of microscopic air bubbles in the tubing [5]. On the other hand, partial obstruction of the catheter by a thrombus can cause attenuation of arterial pulsations and a decrease in the systolic arterial pressure, the diastolic arterial pressure and the average arterial pressure at the same time. Apart from the direct effect of these defects on the values of the systolic and diastolic arterial pressures, an impact on the values of the derived indices mentioned hereinabove can also be observed.

Now, the clinical staff more easily detects a damping factor or attenuation than resonance on the signal displayed on the monitor. In the first case, it usually performs one or more fast flushes of the tubing until the defect disappears.

Various devices, recommendations for use and/or test methods have been proposed for eliminating the resonance phenomenon. In this way, the Accudynamic device [6], now abandoned, manually adjusts the damping factor. For a given measurement configuration, the R.O.S.E. device [7] firmly corrects the dynamic parameters of the measuring assembly by adding a damping factor.

The Gabarith test [8] validates the measuring chain assembly, including the monitor, by its dynamic response to the new state. However, these devices do not consider the fact that the parameters of the hydraulic connection evolve over time. On the other hand, it is difficult for doctors and clinical staff to identify any alteration in the signal appearing unexpectedly and over a random period.

Clinical research studies disclose a transducer located closest to the catheter to minimise distortions of the incident signal due to resonance of the hydraulic connection. However, these recommendations are difficult to execute in current practice, as the artefacts linked to the movements of the patient are more important than in the case where the transducer is at a distance of around 1.5 m from the catheter. Also, this arrangement is less convenient for clinical staff due to immobilisation of the relevant patient.

Studies have also shown the impact of mechanical characteristics of the material of the tubing, especially the static and dynamic Young's modules, on the distortions of the signal. However, even if manufacturers choose a particularly appropriate material, this improves the dynamic performance of the hydraulic connection but fails to eliminate distortions. Also, low-pass filtering usually implemented on the monitors could to a certain extent reduce overestimations due to resonances.

In fact, intensive care unit monitors are generally programmed with a 12-Hz low-pass filter which supplies a smoother arterial pressure curve giving less noise. Also, if the resonance frequency of the hydraulic connection is around 14 Hz, often the case with new tubing and/or those without bubbles, 12-Hz filtering effectively reduces overestimations due to resonances. However, this filtering is carried out to the detriment of natural component of the incident signal having high frequencies, which are eliminated.

Now, it is generally estimated that it is necessary to consider from 5 to 10 harmonics of the fundamental frequency of the signal (of the order of 0.5 to 4 Hz) to describe it correctly, with some specific treatments needing as many as 20 harmonics [9]. The 12-Hz filtering can therefore result in impoverishment of the signal. On the other hand, 12-Hz filtering fails to prevent distortions caused by low-frequency resonances. Now, in case of accumulation of bubbles in the tubing, the resonance frequency can drop as far as 5 or 6 Hz, on which the 12-Hz filtering has no influence.

Finally, some commercially available monitors are equipped with a function for correcting the measured signal as a function of the dynamic characteristics of the hydraulic connection, which must be parameterised in the monitor by an operator. However, clinical staff is not usually trained for this type of adjustment and, if incorrect parameters are sent to the monitor, they risk engendering additional distortions. On the other hand, the resulting correction is effective only over a short time, since the characteristics of the tubing evolve over time.

Document DE 39 27 990 [10] discloses a correction method of the measured signal, consisting of applying a pressure pulse to the tubing outer wall and measuring superposition of the incident arterial pressure signal and the dampened oscillation signal generated by said pulse. Processing of the superposed signal defines the correction parameters of the measured signal. However, this superposed signal is complex and extraction of the correction parameters is therefore delicate. Also, a pressure pulse is hardly capable of defining the damping factor of the connection. Also, this method does not consider artefacts likely to occur during measuring nor the fact that the tubing might consequently contain bubbles which will evolve the necessary correction over time.

Now, the pulse is generated only by action of the clinical staff and, even if the measured signal is properly corrected in a short time after application of the pulse, nothing guarantees that this correction stays effective for a long time. There is therefore a need to improve the quality of an arterial pressure signal measured by the transducer.

An aim of the invention is therefore to provide a method and device which improve, throughout the shelf life of the hydraulic connection, the quality of the measured signal and the reliability of information supplied to the clinical staff. Given the long-held habits by hospital personnel with the conventional device for measuring arterial pressure by arterial catheter, it is preferable to also modify the existing device as little as possible. Naturally, the device should fully respond to demands in terms of sterility and security with respect to the patient, as required for this type of equipment.

According to the invention, a monitoring and, where needed, continuous correction method is proposed for measuring arterial pressure realised by a pressure transducer connected by means of a hydraulic connection to a catheter previously introduced into the artery of a patient, said hydraulic connection sending to the transducer an arterial pressure signal from the patient, called "incident signal" applied to the arterial inlet of the catheter and the transducer transforming the signal transmitted by the hydraulic connection into an electric signal, called "measured signal". Said method is characterized in that it comprises steps of:

determining, from the measured signal, dynamic parameters of said hydraulic connection, said parameters comprising the natural frequency and the damping coefficient of the hydraulic connection, analysis of the frequential content of the incident signal so as to determine the maximal frequency component of said signal, detecting, from said dynamic parameters of the hydraulic connection and, where needed, from the maximal frequency to be transmitted, of one of the following situations:

(a) the aptitude of the hydraulic connection for transmitting the incident signal to the transducer with distortion less than a threshold, (b) the aptitude of the hydraulic connection for transmitting the incident signal to the transducer with distortion greater than said threshold and the possibility of correcting the measured signal, (c) the inaptitude of the hydraulic connection for transmitting the incident signal to the transducer with distortion less than said threshold and the impossibility of correcting the measured signal, said method comprising also the periodic application of mechanical action to the tubing outer wall that forms the hydraulic connection.

The execution of this method does not include the arterial cannulation which has been installed previously in the artery of the patient. Particularly advantageously, said mechanical action comprises percussion of the tubing outer wall that forms the hydraulic connection. Alternatively, said mechanical action comprises a series of sinusoidal stresses of variable frequency applied to the outer wall of the tubing that forms the hydraulic connection.

Preferably, said mechanical action is synchronised with a diastole or is segmented to be synchronised with several successive diastoles. Determining the dynamic parameters of the hydraulic connection can be done from analysis of the measured signal in response to a fast flush and/or to said mechanical action applied to the tubing outer wall which ensures the hydraulic connection and/or from analysis of the frequential content of the signal.

According to an embodiment, detection of one of the situations (a), (b) or (c) comprises comparison of the measured signal and the corrected measured signal as a function of the dynamic parameters of the hydraulic connection. According to another embodiment, detection of one of the situations (a), (b) or (c) comprises the positioning, on a summary table natural frequency-damping factor, of the point representative of the dynamic parameters of the hydraulic connection relative to an area of tolerance determined by the maximal frequency component of the signal used. In the situation (b), the method advantageously comprises the correction of the measured signal as a function of the dynamic parameters of the hydraulic connection. In the situation (c), the method comprises emission of an alert signal, especially light.

Preferably, said alert signal comprises an indication of an action to be undertaken by the clinical staff, such as a fast flush or replacement of the hydraulic connection and/or the catheter. Also, the method can comprise recording of the measured signal, corrected where needed. The method can also comprise transmission of the measured signal, where needed corrected, to a processing system.

Preferably, if the analysis of the frequential content of the incident signal detects spectral slipping and/or a variation of the relative weight of the components of higher frequencies, said step for determining the dynamic parameters of the hydraulic connection is executed so as to update said parameters. Optionally but advantageously, the method further comprises detection of decoupling between the central arterial pressure and the radial arterial pressure of the patient, said detection comprising monitoring of the ratio between the higher harmonics and the lower harmonics of the measured signal and, if said ratio suddenly falls:

execution of a brachial and/or carotid tonometric measurement, determining of the ratio between upper harmonics and the lower harmonics of the brachial and/or carotid pressure signal, the comparison of said ratio with the ratio between the upper harmonics and the lower harmonics of the measured signal.

Alternatively or in addition, the method can also comprise detection of decoupling between the central arterial pressure and the radial arterial pressure of the patient, said detection comprising executing applanation tonometry of brachial/radial and/or carotid arteries, the monitoring of the pulse wave velocity propagation of the patient determined from said applanation tonometry and of the measured signal, and comparison of said velocity with a reference value. In case of impossibility of performing applanation tonometry of the carotid artery, the aortic pressure is evaluated by a transfer function from measuring the brachial pressure. Preferably, each of the two steps for detection of decoupling described hereinabove is conducted; if each of the two detections discloses decoupling of the central arterial pressure and of the radial arterial pressure of the patient, an alarm is issued.

Another object relates to a continuous monitoring and, where needed, correction device of the measurement of the arterial pressure performed by a pressure transducer connected, by means of a hydraulic connection, to a catheter previously introduced into the artery of a patient, said hydraulic connection transmitting to the transducer an arterial pressure signal of the patient, called "incident signal" applied to the arterial inlet of the catheter, and the transducer transforming the signal transmitted by the hydraulic connection into an electric signal, called "measured signal".

Said device is characterized in that it comprises:

a monitoring and correcting module adapted to perform the steps consisting of:

determining, from the measured signal, the dynamic parameters of said hydraulic connection, said parameters comprising the natural frequency and the damping coefficient of the hydraulic connection, analysing the frequential content of the incident signal, so as to determine the maximal frequency component for transmitting said signal, detecting, from said dynamic parameters of the hydraulic connection, and, where needed, from the maximal frequency to be transmitted, one of the following situations:

(a) the aptitude of the hydraulic connection to transmit the incident signal to the transducer with distortion lower than a threshold, (b) the aptitude of the hydraulic connection to transmit the incident signal to the transducer with distortion greater than said threshold and the aptitude of said module for correcting the measured signal, (c) the inaptitude of the hydraulic connection to transmit the incident signal to the transducer with distortion lower than said threshold and the inaptitude of said module for correcting the measured signal, an actuator module, adapted so as to periodically apply mechanical action to the outer wall of the tuning that forms the hydraulic connection.

Said device is integrated into a conventional measuring chain of arterial pressure comprising said catheter, said hydraulic connection and said pressure transducer. The advantage of such a device is to conserve the conventional arrangement adopted in clinics (that is, with transducer away from the catheter) with its known advantages, especially the fact that the transducer is less sensitive to motion artefacts of the patient, as well as maintaining better mobility of the patient. On the other hand, said device rectifies the disadvantages of the conventional arrangement by detecting and, where needed, correcting distortions due to the dynamic characteristics of the hydraulic connection.

The device also ensures permanent follow-up of incidents and quality of the connection, allowing the clinician to know whether he can trust his equipment for measuring arterial pressure. Very easy to install, by default the device does not need to be adjusted by the operator, and then remains fully transparent for hospital staff. Its neutralisation, complete, temporary or for the rest of the service life of the connection, can be done instantaneously by simple pressure on a button.

According to a preferred embodiment, the monitoring and correcting module comprises:

a first processor, adapted to determine the dynamic parameters of the hydraulic connection, analyse the frequential content of the incident signal, detect one of situations (a), (b) or (c) and, where needed, define correction parameters of the measured signal as a function of the dynamic parameters of the hydraulic connection, a second processor, adapted where needed, to continuously correct the measured signal from the correction parameters defined by the first processor.

Particularly advantageously, said first and second processors are connected so as to ensure redundant treatments, reinforcing the safety of the device. The actuator module preferably comprises a piezoelectric actuator or an electromechanical device.

According to an embodiment, the device comprises a wired connection between the monitoring and correcting module and the actuator module, said wired connection being adapted to supply the actuator module with a synchronisation signal with a diastole and/or electric power coming from the monitoring module. According to another embodiment, the device comprises a wireless connection between the monitoring module and the actuator module, said wireless connection being adapted to supply the actuator module with a synchronisation signal with a diastole emitted by the monitoring module. In this case, the actuator module advantageously comprises a rechargeable battery for its power supply. The monitoring and correcting module can be included in a casing connectable between the pressure transducer and a monitor displaying the measured signal.

According to a particular embodiment, the actuator module is included in the same casing as the monitoring module. Alternatively, the actuator module is adapted to be connected to the tubing forming the hydraulic connection, at a distance from the monitoring and correcting module. Particularly advantageously, the device further comprises a processing system adapted to communicate with the monitoring module.

Said processing system can be adapted to process the measured signal, where needed corrected, transmitted by the monitoring module. Said processing system can also be adapted to transmit modification instructions of the operation of said monitoring module to the monitoring module. Said processing system can be included in a portable personal assistant. Said device can also comprise a casing of applanation tonometry for detection of any decoupling between the central arterial pressure and the peripheral arterial pressure.

BRIEF DESCRIPTION OF THE DRAWINGS

Other characteristics and advantages of the invention will emerge from the following detailed description, in reference to the attached drawings, in which:

FIGS. 13A and 13B illustrate respectively aortic and radial pressures in a normal pig and in a pig in a septic shock situation;

DETAILED DESCRIPTION

Figure 1:
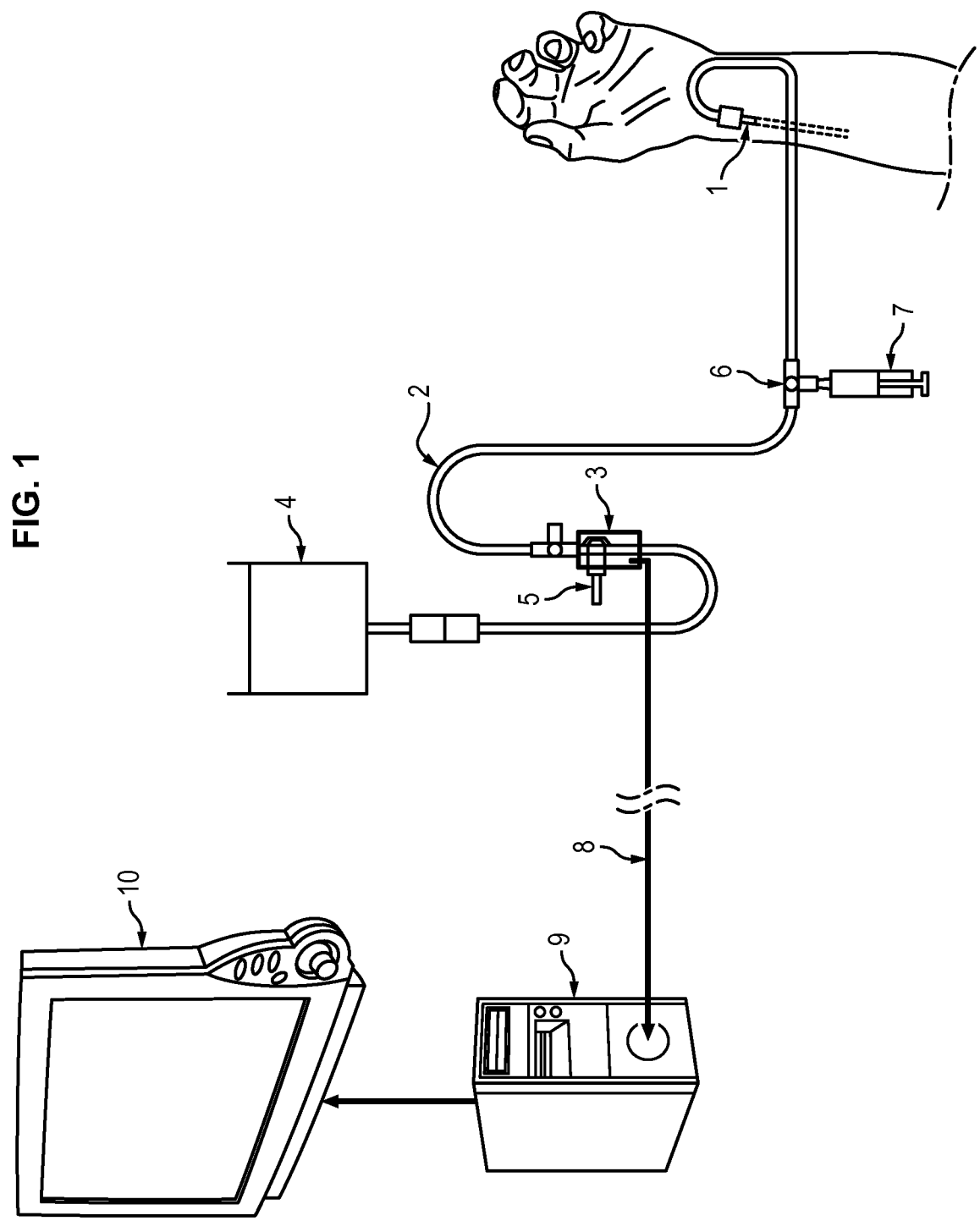
FIG. 1 is a diagram of a conventional device for measuring the blood arterial pressure by arterial catheter of the radial artery.
Figure 2:
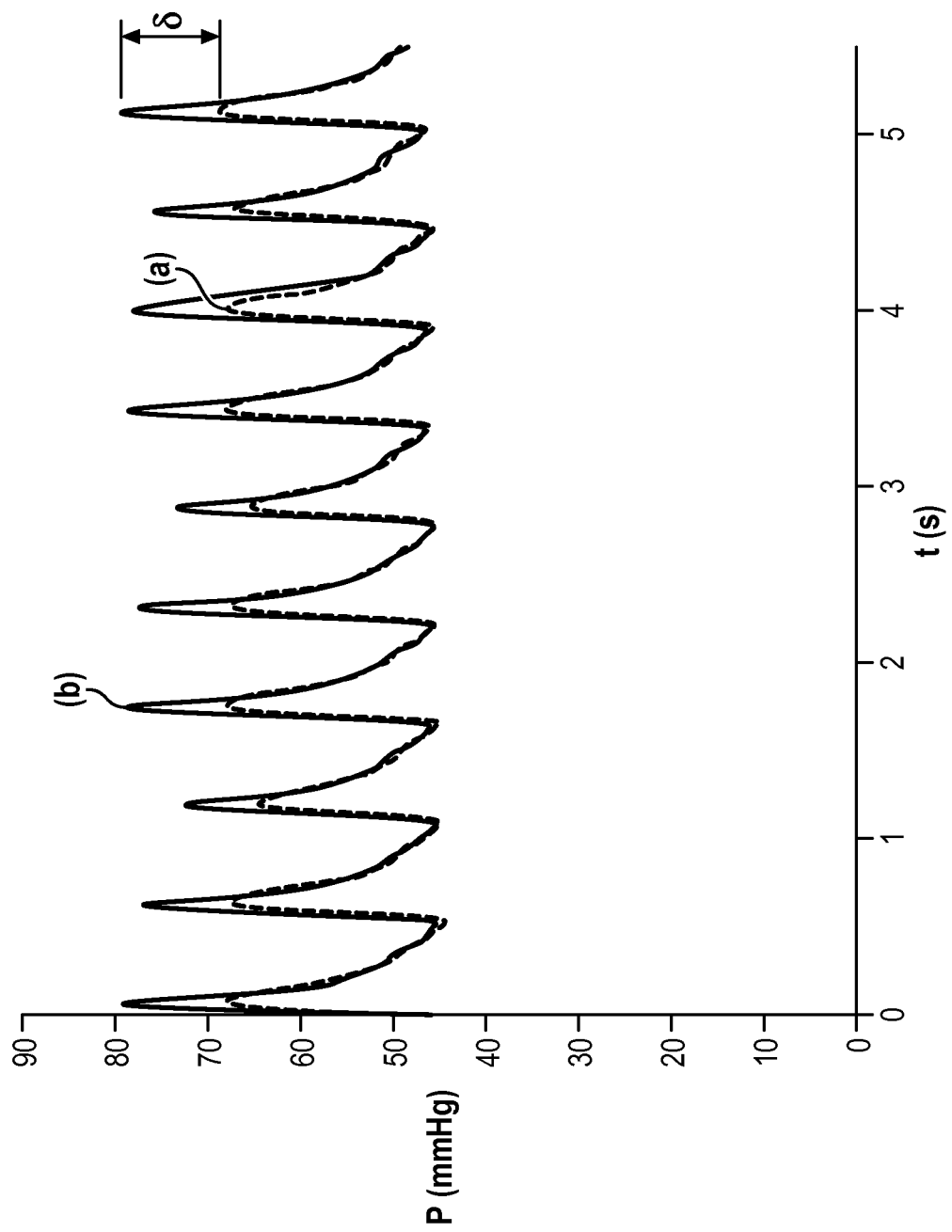
FIG. 2 shows a line of the arterial pressure obtained by a device of the type illustrated in FIG. 1 and a baseline obtained by a catheter-tip pressure transducer located at the level of the arterial inlet.
Figure 3:
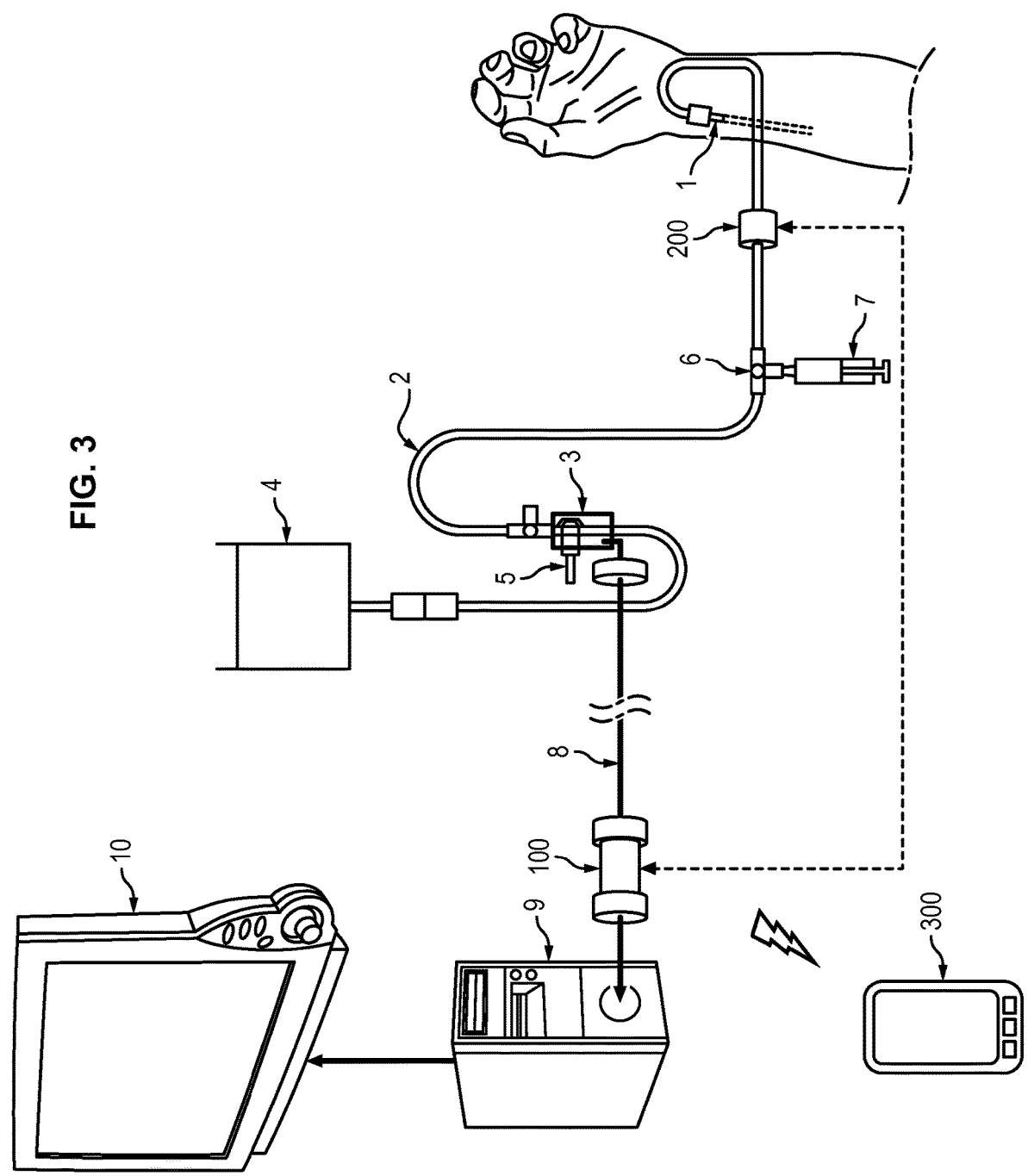
FIG. 3 is a diagram of a device for measuring arterial pressure by radial artery catheter incorporating a monitoring and correction device according to an embodiment of the invention.

FIG. 3 is a diagram of an embodiment of a device for measuring the arterial pressure of the radial artery catheter in which the monitoring device is inserted and, where needed, correction device, mentioned earlier. The components fulfilling the same function as those already described in reference in FIG. 1 have the same reference numerals. The monitoring and correction device mainly comprises a monitoring and correcting module 100 and an actuator module 200, described successively hereinbelow.

Monitoring and Correction Module

Functions Fulfilled by the Monitoring and Correcting Module

The monitoring and correcting module 100 comprises electronic components and embedded computer applications for fulfilling in real time the following functions which perform monitoring and, where needed, correction of the blood arterial pressure measurement. One function consists of characterising the intrinsic dynamic parameters of the hydraulic connection 2, specifically its natural frequency $f_0$ and its damping coefficient z. Different methods, some of which utilise the actuator module 200 which allow this characterisation, will be described hereinbelow.

Another function comprises frequential analysis of the incident arterial pressure signal to determine the maximum frequency component (noted fh) which the hydraulic connection must transmit correctly to provide clinical staff with an accurate representation of the arterial pressure of the patient. Another function comprises estimation, from the parameters ($f_0$, z and optionally fh) determined previously, of the aptitude of the hydraulic connection for reproducing the incident signal with a given range of distortion.

More precisely, this estimation phase detects one of the three following situations:

(a) a situation in which the hydraulic connection is capable of transmitting the incident signal with distortion lower than a determined tolerance threshold, for example distortion lower than 5% (in this case no correction of the measured signal is necessary);

(b) a situation in which the hydraulic connection transmits the incident signal with distortion greater than said tolerance threshold, but with the possibility, for the monitoring module, of correcting the measured signal;

(c) a situation in which the hydraulic connection transmits the incident signal with distortion greater than said tolerance threshold, but without the possibility, for the monitoring module, of correcting the measured signal.

Another function likely to be used by the monitoring module 100 is the automatic correction of the measured signal when possible (that is, essentially in situation (b)), by using the dynamic parameters of the hydraulic connection determined in the characterisation phase. Another function comprises detection of measuring artefacts and various incidents which might occur on the hydraulic connection and on the catheter, and such as to question the pertinence of information given by the monitor. Another function comprises providing clinical staff with information on the current state of the hydraulic connection and on any need for corrective action on its part (typically, fast flush or replacement of the tubing and/or of the catheter). This information is preferably supplied by means of a simplified man-machine interface, for example consisting of an indicator light which can take on a different colour as a function of each of situations (a), (b) and (c).

Advantageously, the clinical staff can choose one of the three following operating modes of the monitoring and correcting module:

a mode called "active", for example the default mode, in which the monitoring and correcting module analyses the incident signal and the dynamic parameters of the hydraulic connection, evaluates the capacity of the connection for faithfully reproducing the incident signal, optionally corrects the measured signal and if needed alerts for intervention of the clinical staff;

a mode called "passive", in which the monitoring and correcting module functions as in the active mode, with the exception that it does not modify the measured signal (especially, it makes no correction, even when this would be necessary and doable); only the monitoring function is active;

a mode called "neutral", in which the monitoring module is fully deactivated.

Architecture of the Monitoring and Correcting Module

Figure 5:
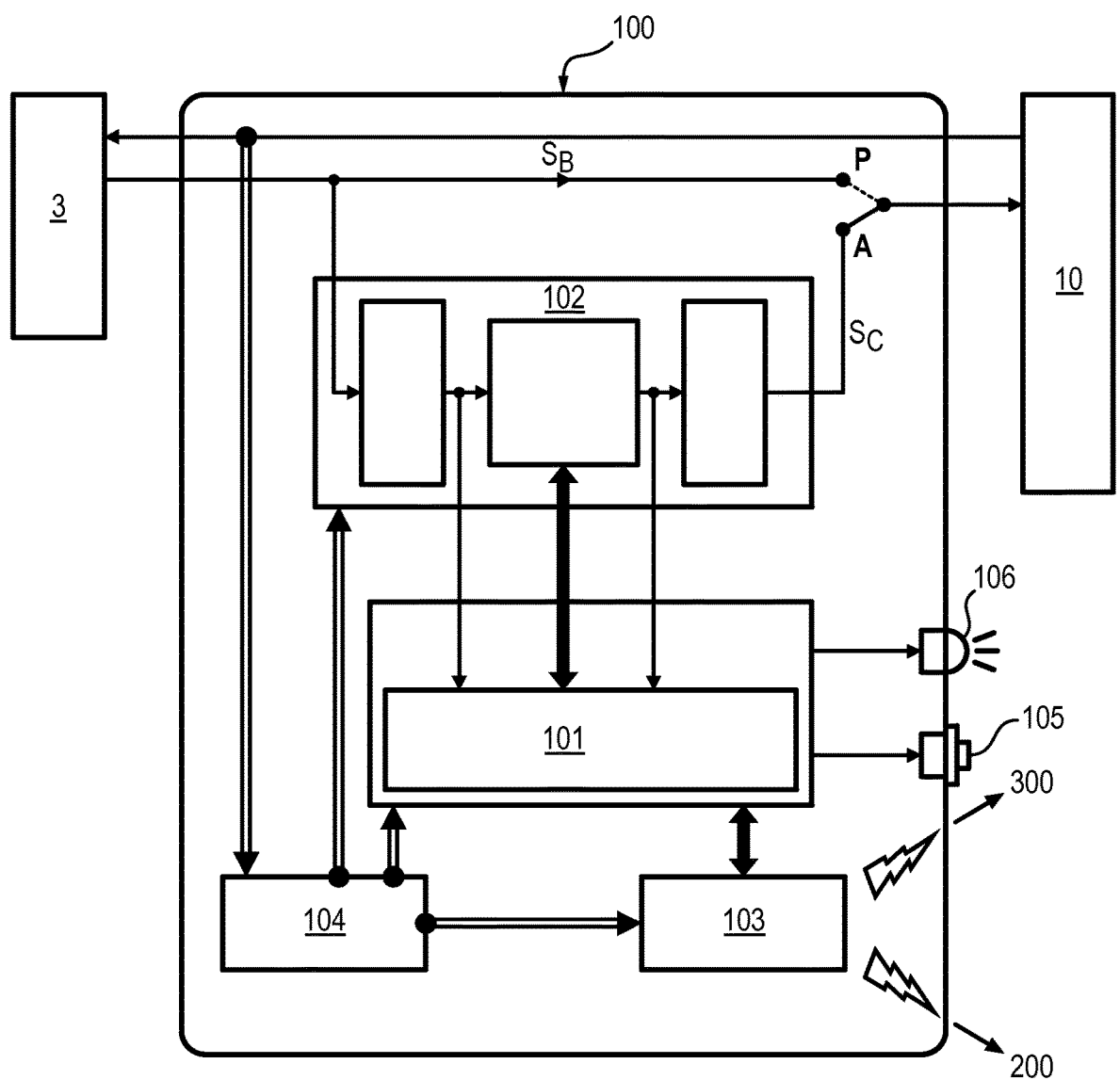
FIG. 5 diagrammatically illustrates the architecture of the monitoring and correcting module.

Particularly advantageously, the monitoring and correcting module 100 comprises two processors capable of communicating with each other and each of which ensures some of the functions explained hereinabove. This architecture is illustrated diagrammatically in FIG. 5. The module 100 is interposed between the transducer 3 and the pre-amplifier 9 of the monitor 10. The transducer 3 transmits a raw measured signal, noted $S_B$, to the module 100. The alternative between the passive and active modes is shown diagrammatically by the commutation between the markers P and A.

A first processor 101 performs the majority of processing the measured signal. This first processor 101 is configured to characterise the dynamic parameters of the hydraulic connection. In this respect, the first processor 101 analyses the response of the hydraulic connection to the fast flushes initiated by the clinical staff according to current monitoring protocol and/or mechanical actions stressing the tubing, exerted periodically by the actuator module 200.

The first processor 101 also conducts frequential analysis of the incident signal and its evolution over time, especially for determining the fundamental frequency ff and the other significant components (contributing to analysis) of said signal. From these analyses the first processor 101 then estimates the aptitude of the hydraulic connection for accurately reproducing the incident signal in a given tolerance range. As a function of situation (a), (b) or (c), the first processor 101 defines any correction to be made to the measured signal.

In this way, in situation (a) the first processor 101 provides the monitor with the raw signal, without correction. In situation (b) the first processor 101 determines the new correction parameters to be applied and updates them in a second processor 102 which, as will be explained later, is intended to correct the measured signal. Finally, in situation (c) the first processor 101 delivers an alert to clinical staff by means of the simplified man-machine interface mentioned earlier. By default, in this case it supplies the monitor with the raw version of the signal.

Said first processor 101 also performs early detection of possible drift of the dynamic parameters of the hydraulic connection if a substantial variation of the spectral content of the measured signal is observed (spectral slipping and/or variation of the relative weight of the components of upper frequencies). In this case, a characterisation sequence of the connection can be initiated in anticipation. Said first processor 101 also conducts detection and follow-up of events (motion artefacts, obstructions of the catheter, etc.) occurring during measuring and records them in a log which is saved throughout the shelf life of the tubing.

The first processor 101 also communicates with the actuator module 200 via a wired connection or via a wireless connection. If appropriate, the first processor 101 also communicates via a wireless connection with a remote processing system 300. For this purpose, the monitoring and correcting module 100 comprises a communications management module 103 which uses radiofrequency technology for example to communicate with the actuator module 200 and/or the processing system 300.

The monitoring and correcting module comprises a second processor 102 dedicated to continuous correction of the measured signal and in active mode A transmits the corrected measured signal $S_C$ to the monitor 10 by means of the preamplifier 9. The correction parameters are determined by the first processor 101 which updates them periodically in the second processor 102 to reflect the variations over time of the parameters $f_0$ and z of the hydraulic connection. The second processor 102 can also carry out some of the monitoring functions of the hydraulic connection, such as detection of artefacts. However, if an event is detected and needs substantial processing, the first processor 101 is requested.

Power consumption is administered by a power management module 104. The monitoring and correcting module 100 is preferably fed by the field voltage supplied by the monitor 10 to the resistive bridge of the pressure transducer 3. Now, this source has limited capacity, and needs a particularly economic design in terms of energy efficiency of the monitoring and correcting module.

Such performance can be attained by carefully selecting the architecture of both processors 101, 102 and the actions they must ensure. In this respect, the second processor 102, which is constantly active, is dedicated to tasks which use minimal power. Its technology is selected consequently (programmable analogue component, for example). By contrast, the first processor 101 is dedicated to digital processing of the signal, requiring intensive work, but it operates discontinuously. It is based for example on DSP technology ("Digital Signal Processor").

The first processor 101 is requested only during important events (fast flushes, artefacts) and/or on a periodic base selected for updating the characterisation of the hydraulic connection (purely by way of indication, every half hour, for example). So, the duration of operation and calculations is limited relative to that of the periods of inactivity (sleep mode allows very low power consumption). Consequently, average power consumption of the monitoring and correcting module 100 stays very low, with localised peaks corresponding to the processing periods of the signal. Also, the monitoring and correcting module 100 can comprise an energy reserve which capitalises on the permanent but limited source of power supplied by the transducer feed by loading a buffer storage adapted to respond to specific power needs. Said power source can also serve to feed the actuator module 200, in some embodiments to be described later.

Also, the first and second processors 101, 102 are each capable of verifying, on the one hand, the effective operation of the other processor and, on the other hand, the coherence of some results supplied redundantly by the two processors. This ensures the security of the monitoring and correcting module 100. Naturally, the monitoring and correcting module could be implemented with any other architecture than that described hereinabove, however the functions mentioned earlier are fulfilled.

Figure 4:
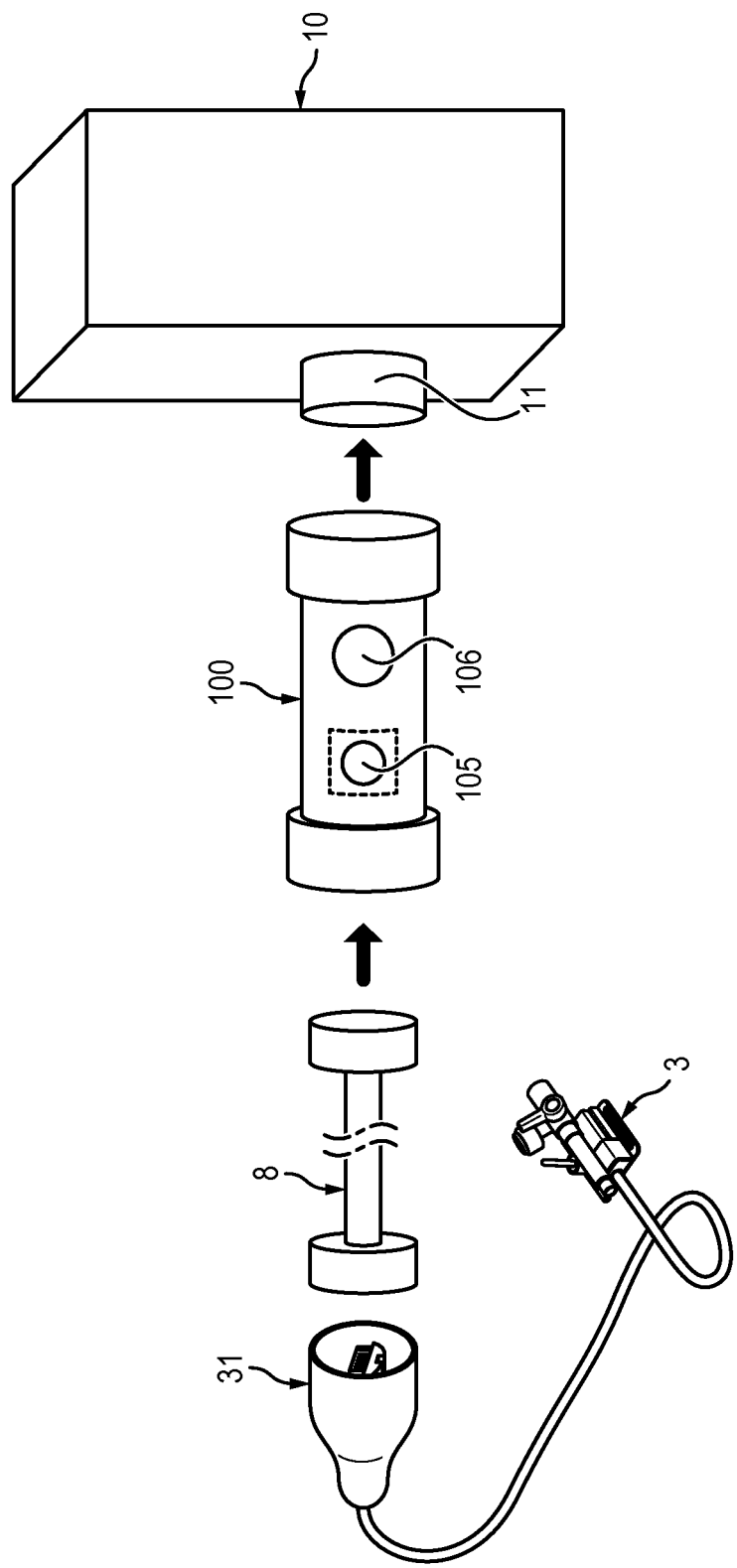
FIG. 4 is a diagram illustrating implantation of the monitoring and correcting module in the existing measuring chain.

The monitoring and correcting module is included in a miniaturised casing which ensures protection of processors and comprises connectors appropriate for interconnecting the module to the existing measuring device. As is evident from FIG. 4, the monitoring and correcting module 100 is connected advantageously between the cable 8 connected to a plug 31 of the transducer 3 and the plug 11 of the monitor 10. In this way, the monitoring and correcting module integrates easily into the existing measuring chain, without generating additional bulk.

Said casing can also incorporate a simplified man-machine interface, comprising an indicator light 106 for producing a different colour according to situation (a), (b) or (c), as well as a push button 105 for selecting the active, passive or neutral mode. For example, the indicator light 106 is green in situation (a), orange in situation (b) and red in situation (c). Said module is preferably designed not to be discarded after single use in a patient but to be reutilised. To this effect, the casing must be able to be sterilized by techniques currently used in hospital.

Actuator Module

The actuator module 200 is intended to apply mechanical action to the tubing so as to excite the hydraulic connection, the measured signal then being analysed by the monitoring module 100 to deduce therefrom the dynamic parameters of the connection. Preferably, said mechanical action is applied in the vicinity of the catheter 1. According to an embodiment, the actuator module 200 generates a pulse intended to provide brief excitation on input of the hydraulic connection 2. According to another embodiment, the actuator module 200 generates a brief series of sinusoidal loads of variable frequency.

More generally, the actuator module 200 can generate any sequence of short-term mechanical loads and capable of characterising the hydraulic connection 2 without considerably perturbing the arterial pressure signal. It is possible to combine said embodiments and excite the hydraulic connection with different types of mechanical actions. Therefore, one can advantageously use a pulse to determine the natural frequency $f_0$ of the connection (percussion method) and a series of sinusoidal loads of variable frequency to determine the damping coefficient z of the hydraulic connection (harmonic method).

Under the effect of the mechanical action of the actuator module 200, the hydraulic connection 2 provides a response characteristic of a system of the second order and dependent on its dynamic parameters. This response is superposed on the incident signal to provide a complex signal which is measured and analysed by the monitoring module 100 which deduces therefrom the preferred dynamic parameters.

According to an advantageous embodiment, the mechanical action is synchronised on a diastole, corresponding to a signal portion whereof the frequential content enables easier analysis than for other segments of this signal. To this effect, the monitoring module 100 (more precisely, in the case of bi-processor architecture, the first processor 101 described hereinabove) sends the actuator module 200 a synchronisation signal which triggers the mechanical action during a diastole. Sending this synchronisation signal can be done either via a wired connection or via a wireless connection.

Optionally, depending on the duration of the series of mechanical loads, the latter could be decomposed into several sequences distributed over several successive diastoles.

The actuator module 200 comprises an actuator arranged to clamp the tubing 2, and make mechanical contact with the external wall of the latter, without significantly deforming it. The mechanical action generated by the actuator causes pressure variation in the saline contained in the tubing. According to an embodiment, the actuator is an active piezoelectric element. In this case, the source of electric power applies voltage between the metallised faces of the piezoelectric ceramic, which deforms as a consequence and transmits a deformation stress to the tubing via mechanical contact.

The mean power consumption of the actuator module 200 is very low, since the latter operates periodically only. Therefore, by way of indication, mechanical action is initiated on the hydraulic connection according to a half-hour period, the duration of said action being a few milliseconds (percussion method) to a few seconds (harmonic method). For this purpose, the actuator module 200 can comprise an internal power source, in the form of a battery, preferably rechargeable by a contactless device (induction), or else external, by means of the wired connection with the monitoring module 100. According to other embodiments, the actuator can be an electromechanical device comprising a coil and a solenoid, or more generally any device for translating an electric signal into mechanical stress.

Said module 200 is preferably designed to not be discarded after single use in a patient but to be reutilised. For this purpose, the actuator module 200 must be able to be easily mounted on and dismounted from the tubing 2. It must also be able to be sterilised by techniques currently used in the hospital.

According to an embodiment, the actuator module 200 is installed at a distance from the monitoring and correcting module 100. Such is the case in FIG. 3, where the actuator module 200 is placed near the catheter while the monitoring and correction module 100 is located near the pressure transducer 3. This implementation is advantageous for processing the signal. In fact, the distance between the point of application of the mechanical actions and the pressure transducer makes characterisation of the dynamic parameters of the hydraulic connection easier.

Figure 6:
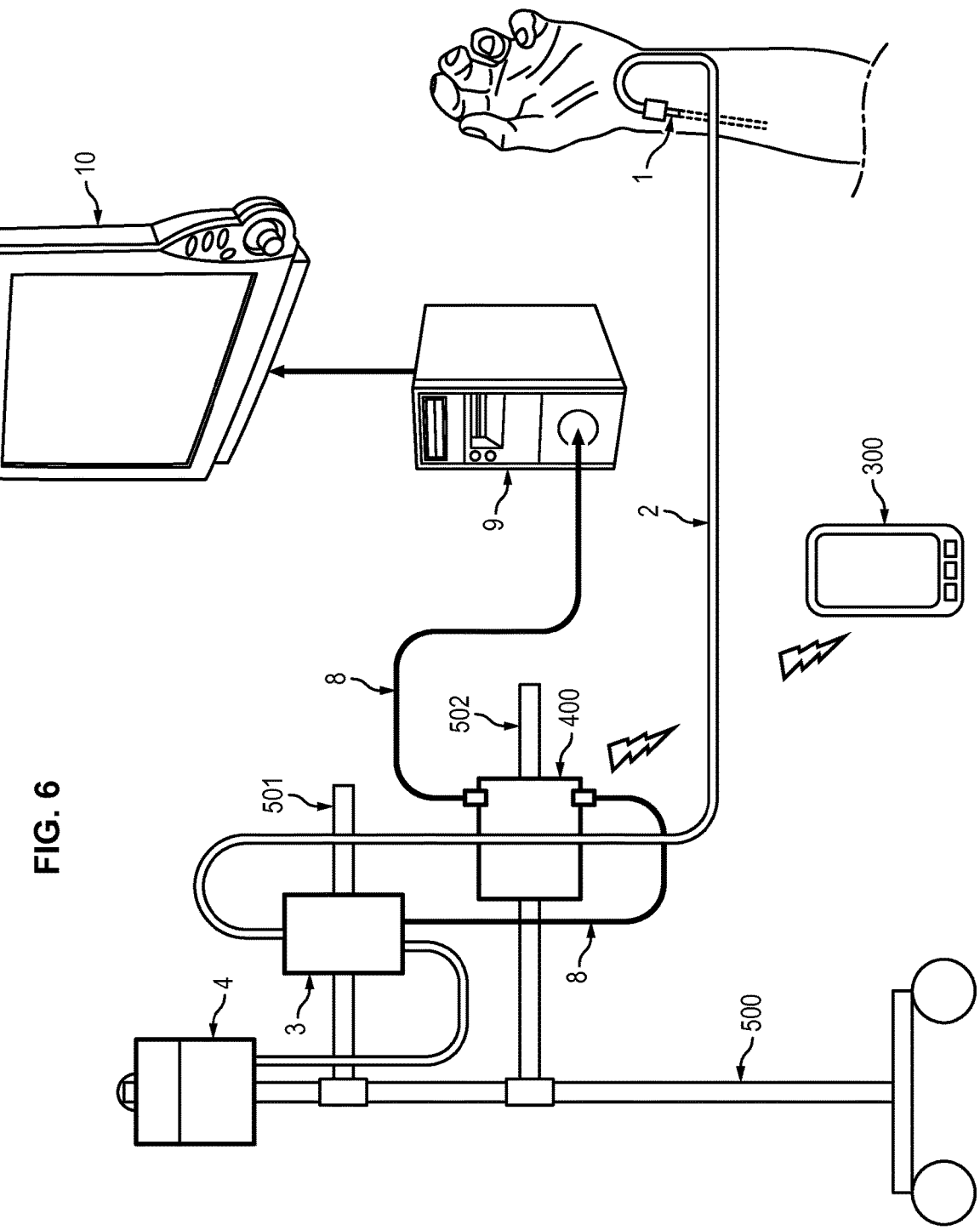
FIG. 6 is a diagram of a device for measuring the arterial pressure by the radial artery catheter incorporating a monitoring and correction device according to another embodiment of the invention.

According to another embodiment, illustrated in FIG. 6, the actuator module and the monitoring and correcting module are installed in the same casing 400. In this case, the casing 400 is installed near the pressure transducer 3. For example, the transducer 3 and the casing 400 are installed on a backplate 501, 502 of an infusion pole 500 which supports the saline bag 4.

The tubing forming the hydraulic connection 2 is locally gripped in the casing 400 so as to be in contact with the actuator module. The casing 400 is connected electrically on the one hand to the transducer 3 and on the other hand to the preamplifier 9 of the monitor 10 by electric cables 8. It is fitted for this purpose with standard electrical plugs adapted to these cables.

An advantage of this implementation is that since the entire device is remote near the transducer, it frees up the end of the tubing to the side of the catheter 1, which is a sensitive zone vis-à-vis the risks of nosocomial infection. Also, this implementation increases comfort for the patient and hospital staff who might feel embarrassed in the presence of an independent actuator placed near the arterial line.

Also, the casing 400 simplifies feed of the monitoring and correcting module and of the actuator module by enabling joint supply, because of the proximity of both modules.

Similarly, the transfer of information between the two modules is simplified. The casing 400 also makes for easy passage of electric cables connecting the corrector to the transducer and monitor. Finally, the user interface of the monitoring and correcting module comprising the status light and the illuminated push-button for mode selection can be installed on the front face of the casing 400 so as to be at eye level of the clinical staff.

Remote Processing System

Advantageously but optionally, the monitoring device can also comprise an remote processing system 300, for example incorporated into a portable personal assistant. Said processing system 300 preferably communicates with the monitoring module 100 via a wireless connection and carries out operations complementary to monitoring and control operations. Therefore, the processing system 300 can process the measured signal and deduce therefrom the derived indices of the systolic arterial pressure described earlier.

Said system can also display the arterial pressure plottings, record them to ensure the traceability of measurements and/or perform quality follow-up. In particular, it can produce detailed display of different curves and parameters in graphic and/or digital form, for example:

curves of raw and corrected arterial pressure, to observe the lines showing over- or under-estimations, derived indices $\Delta PP$, dP/dt max, situation of the hydraulic connection relative to its limits in reproduction of the signal in a given tolerance, evolution over time of the dynamic parameters of the connection, log of events (fast flushes, obstructions, various artefacts . . . )

Said system can also perform calibration and test operations of the monitoring device. In a special adjustment mode, accessible by password, it can also modify some parameters of the monitoring module (especially tolerance thresholds) and update the versions of the software embedded in said module. The processing system 300 can be run, with adapted software, on a device of Personal Digital Assistant (PDA), portable computer or specific apparatus type. It is fitted with a graphic display monitor and an input unit (keyboard, touch screen, etc.) allowing the user to interact with the software. The different methods for processing the signal likely to be used by the monitoring module will now be described in greater detail.

Determination of Dynamic Parameters of the Hydraulic Connection

This determination uses different methods each having strengths and sometimes weaknesses. For this reason, the monitoring device is based on the values obtained by preferably setting a confidence index for each of them and sets up an output result of this method.

Percussion Method Using Fast Flushes

Figure 7:
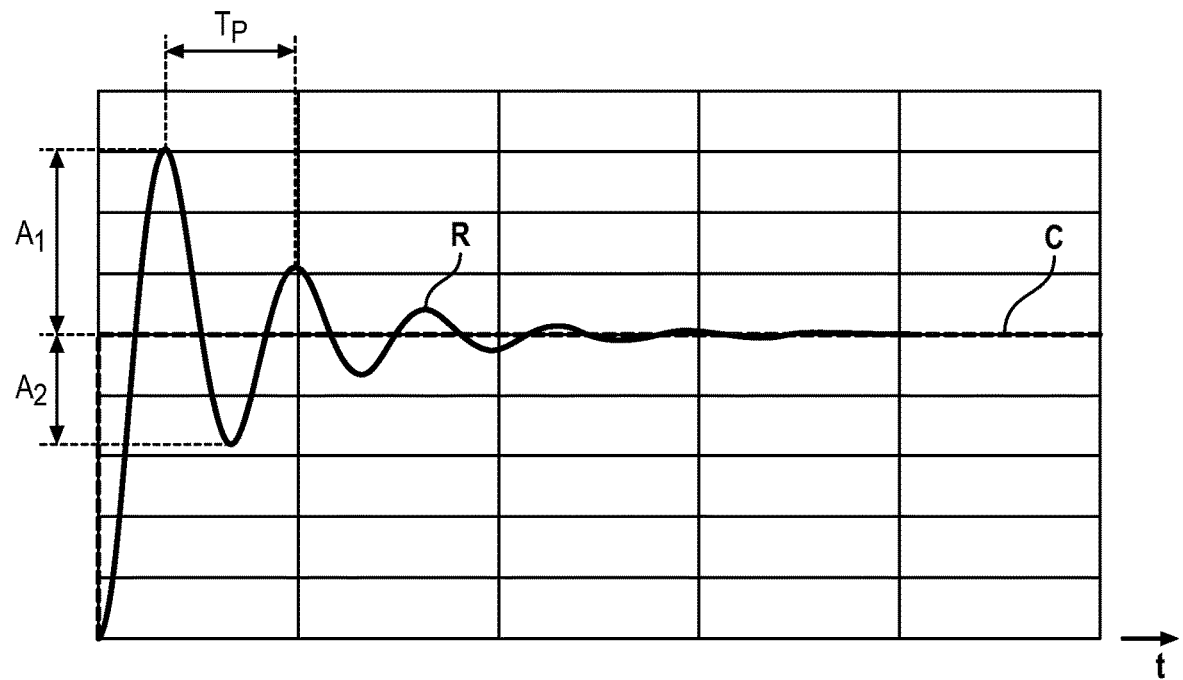
FIG. 7 illustrates the response curve to a setpoint in the form of an echelon, employed in a method known as percussion for determining the dynamic parameters of the hydraulic connection.

Percussion analysis consists of sending a signal echelon at input of the system, and observing how the latter evolves at output. In reference to FIG. 7, application of a setpoint signal C in the form of an echelon causes a response signal R. The setpoint return characteristics (overruns $A_1$, $A_2$ and oscillation frequency fp which is the inverse of the period Tp) find the dynamic parameters of the system, specifically the damping factor z and the natural frequency $f_0$ because of the following formulas:

$$z = \frac{1}{\sqrt{1 + \left(\frac{\pi}{\ln(A_1/A_2)}\right)^2}}$$

and $$f_0 = \frac{f_p}{\sqrt{1-z^2}}$$

This method therefore uses the fast flushes initiated by the clinical staff and forming part of the protocol, which provide a source of echelons from which the method can be implemented. The response to the "fast flush" echelon is closely mingled with the haemodynamic signal of the patient, and therefore an extraction operation has to be performed before proceeding with the analysis indicated hereinabove. This extraction is done by dissociating, on the one hand, the excitation signal of the fast flush and the response of the system to this fast flush, and on the other hand the incident arterial pressure signal.

In this way it enables precise and robust determination of the dynamic parameters $f_0$ and z of the hydraulic connection. However, to the extent where the fast flushes are not always carried out regularly (the interval can last 8 h or even more), or sufficiently forcefully, and to the extent where tubing evolving over several hours without fast flush, different phenomena (ex.: microscopic air bubbles or other) can lead to a significant drift of $f_0$ and z, without the fast flush showing such, percussion analysis based on fast flushes is preferably used in combination with other methods of analysis. Therefore, for example, initial estimation of $f_0$ and z can be drawn from extraction of the response of the hydraulic connection to these fast flushes, then refined by one of the methods described hereinbelow.

Percussion Method Using the Actuator Module

This method is similar to that using the fast flushes, but in this case the percussion is triggered by the actuator module in the form of a brief mechanical pulse, on a regular time basis, which recognises $f_0$ and z between two fast flushes of the system. It rectifies some disadvantages of the preceding method based on the fast flushes, especially by offering implementation periodicity. As for the preceding method, it also needs extraction. However, because triggering of the pulse is controlled by the monitoring module, the action can take place in a less uneven period of the signal, for example diastole. This method is particularly advantageous for calculating the natural frequency $f_0$.

Harmonic Method Using the Actuator Module

This method is particularly precise and reproducible and is therefore preferably used, optionally combined with one of the preceding methods. Harmonic analysis consists of sending a series of sinusoidal signals of variable frequency at the inlet of the hydraulic connection.

Figure 8:
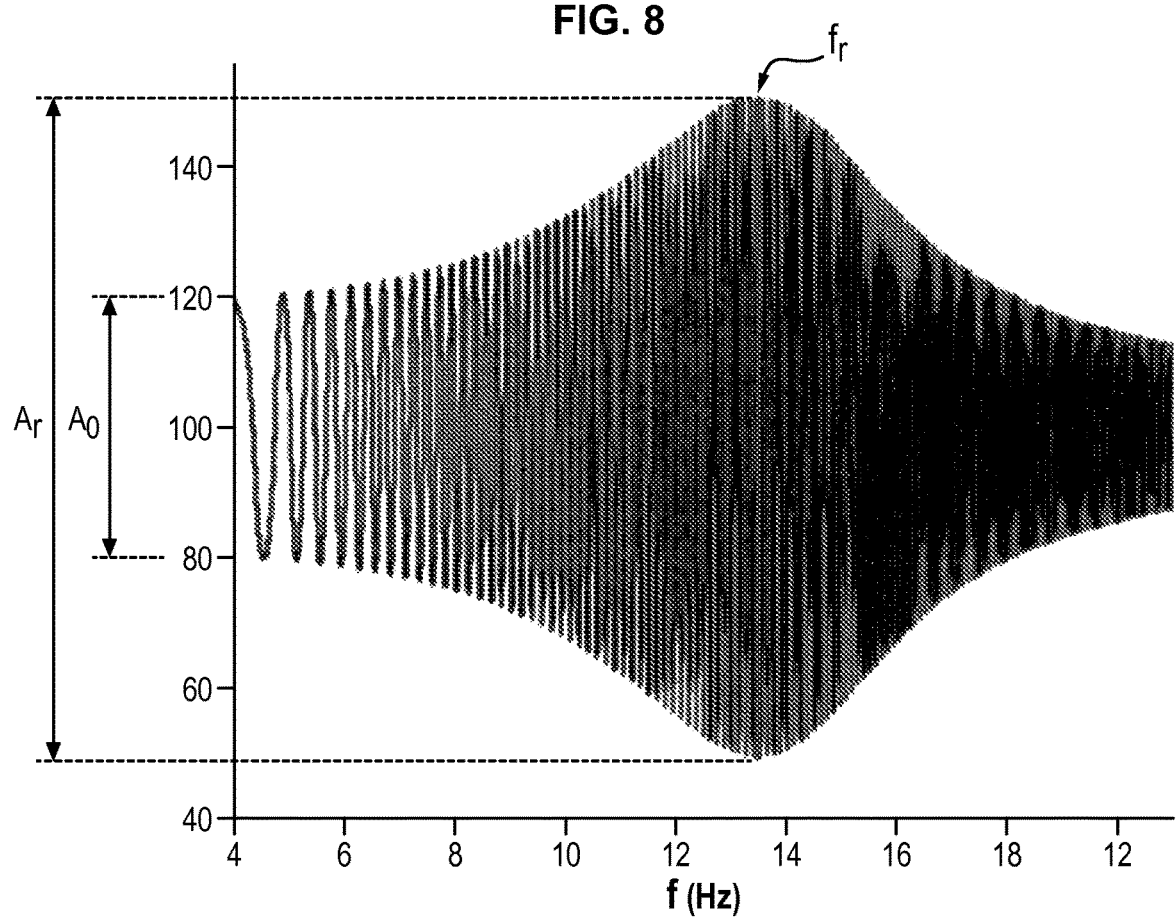
FIG. 8 illustrates a response curve to a series of mechanical sinusoidal stresses of variable frequency, employed in a method called harmonic for determining the dynamic parameters of the hydraulic connection.

As illustrated in FIG. 8, the result at the outlet is a curve characterized by a maximum of amplitude $A_r$ at the resonance frequency fr. These characteristics can find the dynamic parameters of the hydraulic connection, via the formulas:

$$z = \sqrt{\frac{1 - \sqrt{1 - (A_0/A_r)^2}}{2}}$$

and $$f_0 = \frac{fr}{\sqrt{1-2z^2}}.$$

This method needs generation of a series of sinusoidal waves of variable frequency having greater perturbation for the measuring system. Consequently, said method can require segmenting of the mechanical action into several rounds distributed over successive diastoles. To make analysis easier, this method could advantageously be synchronised by the corrector to occur in a minimally perturbed phase of the signal, such as a diastole.

Analysis of the Evolution of the Measured Signal Spectrum

The principle of this method rests on the fact that the generation of resonances at the hydraulic connection impacts the spectral content of the measured signal. Via appropriate processing, the system can detect resonance and evaluate its parameters ($f_0$ and z) [11]. The results coming from this method consolidate the measurements coming from other methods and detect the evolution of dynamic characteristics of the hydraulic connection.

Determination of the Frequential Content of the Incident Signal

Figure 9:
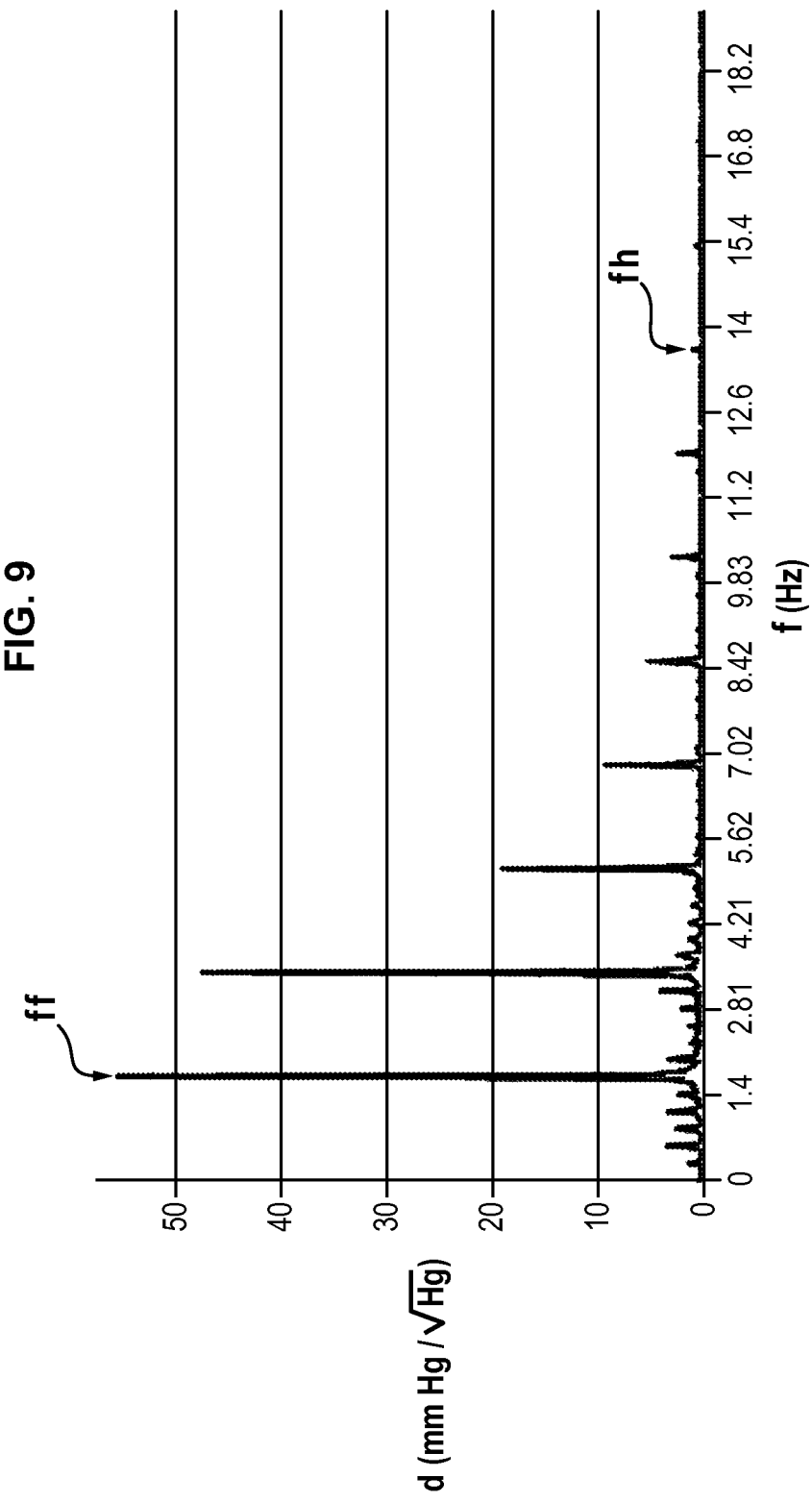
FIG. 9 illustrates the line of the frequential spectrum of an incident signal, for determining the fundamental frequency of said signal (ff) and the maximal frequency component to be transmitted (fh)

This determination is made on the basis of FFT analysis of the incident signal on the one hand to set the value of the fundamental frequency ff and on the other hand the value of the maximal component to be transmitted (fh). fh is set by evaluating the extent of the harmonics of significant amplitude (contributing to the analysis). In this respect, the majority of authors agrees on 5 to 10 harmonics. Purely by way of indication, FIG. 9 illustrates a curve of the spectral density of the pressure signal as a function of frequency.

Estimation of the Aptitude of the Hydraulic Connection for Accurately Reproducing the Incident Signal This estimation is based on the previous determination of $f_0$, z and, where needed, fh. Knowing $f_0$ and z suffices to characterise the hydraulic connection. To correctly evaluate the capacity of said connection for correctly reproducing a given incident signal, several methods are possible.

Figure 10:
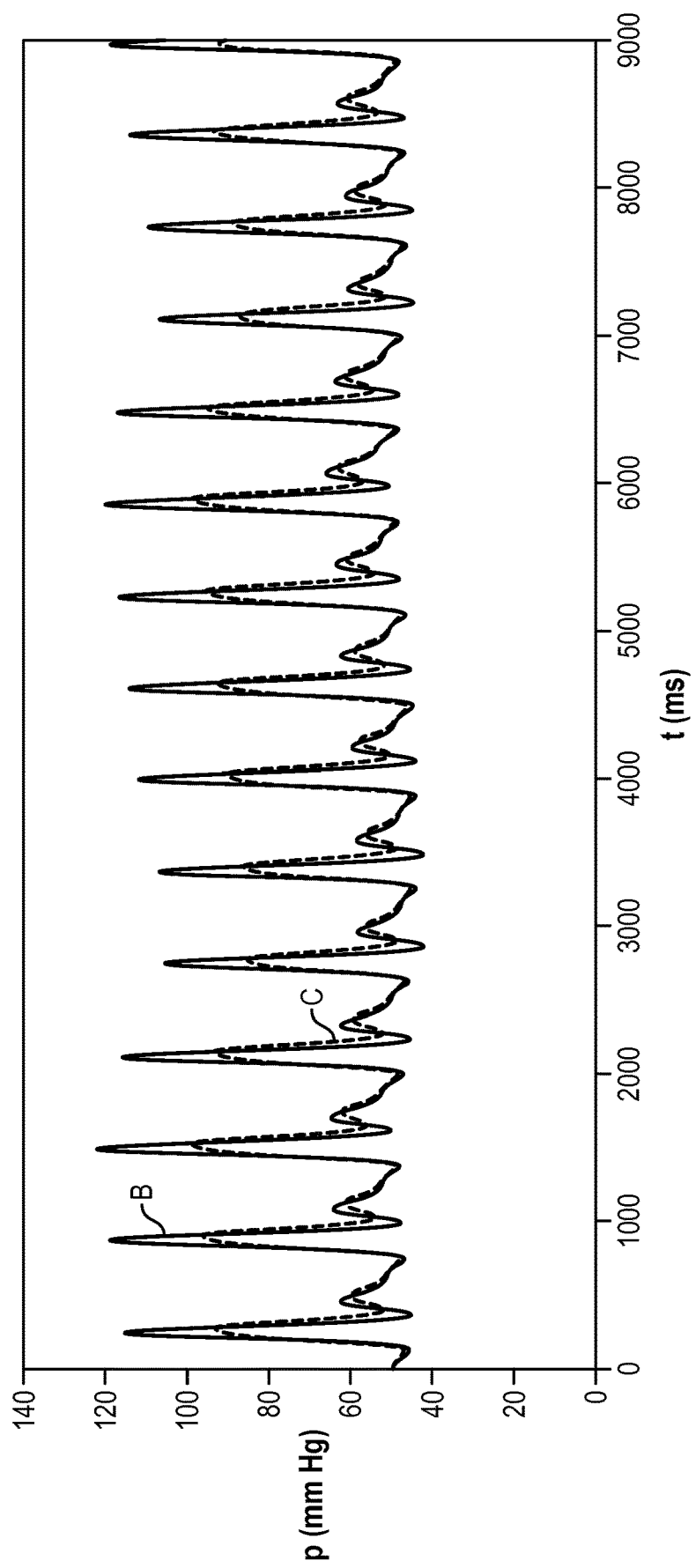
FIG. 10 shows the plotting of a raw measured signal and of a corrected measured signal, comparison of which determines overestimation of the systolic pressure introduced by a resonant hydraulic connection.

A first method comprises application, via software, of correction of the distorted incident raw signal followed by comparative study of both signals (raw and corrected). FIG. 10 shows a portion of signal acquired immediately after a fast flush, revealing the raw signal B and the corrected signal C, which allowed determining by percussion analysis the characteristics of the hydraulic connection connecting the catheter to the transducer and reconstructing the signal exempt of deformations.

A second method has been put forward by several authors [12]. Said method can be illustrated by preset templates or summary tables revealing, in a graphic made in the plane ($f_0$, z), zones where a maximum frequency component fh could be or not be reproduced with distortion lower than 5% for example. The positioning on the summary table of parameters of the hydraulic connection ($f_0$, z) and of the maximum frequency component of the incident signal (fh) determines whether the device is capable or not of processing the signal of the patient.

Figure 11:
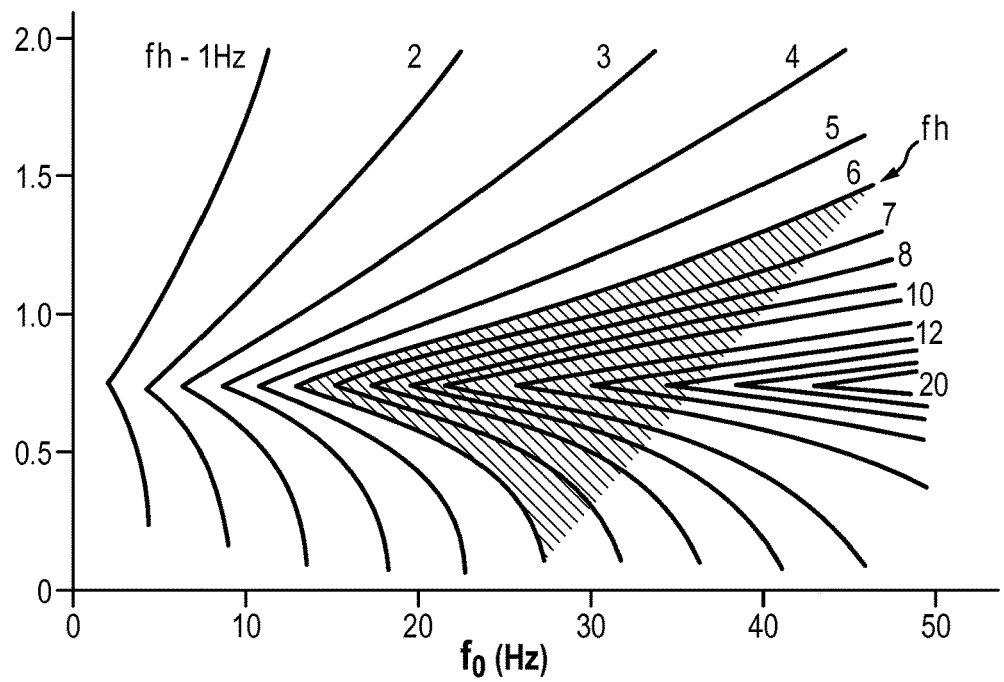
FIG. 11 illustrates the execution of a method for estimation of the aptitude of the hydraulic connection for reproducing the incident signal with distortion lower than a given value.

FIG. 11 shows an exemplary embodiment of said method. For a maximum given frequency fh to be transmitted (fixed here, by way of example, at 6 Hz), the area inside the curve corresponding to this frequency represents, in the plane ($f_0$, z), all the values compatible with the tolerance of ±5% (hatched on the diagram). The two methods described hereinabove are based on different methods, but must end up in coherent results. In this case, estimation of the quality of the hydraulic connection is possible, whereas in the contrary it is necessary to redo characterisation of the hydraulic connection.

Monitoring of the Hydraulic Connection

One of the functions of the monitoring device consists of ongoing monitoring of the entire system for measuring arterial pressure, with the aim of detecting those situations which might compromise reliability of the indications displayed on the patient monitor. Said situations are the following. On the one hand, artefacts of different categories can be detected.

These can be motion artefacts due to changes in position of the patient, especially those parts of the body near the measuring system (example: wrist in case of radial artery catheter); artefacts due to interactions with the exterior, for example when clinical staff inadvertently knock the tubing, which becomes a jerk on the pressure plotting. These artefacts are phenomena affecting measurements temporarily. The monitoring device detects them and informs the clinical staff, for example by way of the status light briefly flashing red.

Another function of the monitoring device is to detect abnormal attenuation of the incident signal. The attenuation phenomenon of the signal, already described in the literature [13], results in a plotting that is often notably weakened and sometimes wrongly qualified as a damping, a different phenomenon from which it has to be distinguished. In fact, an extra damping of the hydraulic connection can occur when the damping coefficient z attains an excessively high value, due to accumulation of microscopic air bubbles in the tubing, for example.

This phenomenon is characterized by the monitoring device and in some cases can be the subject of an automatic correction and/or an alert for the clinical staff to the need for intervention. However, in the case of the attenuation phenomenon, the origin of the defect is not in the for example itself, but in the catheter or the artery of the patient where a temporary obstacle (example: thrombus, . . . ) can appear, or even precede catheterisation (for example, atheromatous plaque in the arteries of the patient). The result is temporary or ongoing obstruction, causing considerable attenuation of the signal and making measuring unworkable.

This type of defect cannot be corrected automatically by the monitoring device. However, the monitoring function of this device detects this situation and informs the clinical staff by illuminating the status light, for example in steady red, superposed on a more intense periodical flash of light intended to get attention to urgent intervention. This intervention most often implies a fast flush which can eliminate the defect.

In this case, the device detects the return to normal with a status light lit up green or orange. In the event where the defect has not disappeared or reappears after some time, the device again requests intervention which can be more substantial, such as replacement of a catheter. The advantage of detection made by the monitoring device is not waiting until the plotting is completely attenuated before an alert is given. On the other hand, the monitoring device can consign any incidents to measuring arterial pressure. Therefore, each incident which has temporarily or durably affected the reliability of measurements over the shelf life of the measuring device is recorded in a log stored in the monitoring module. This log can be consulted via the processing system mentioned earlier.

On catheter removal, for example, the log can be reinitialised by a command from the processing system or, for example, sustained pressing of the mode button. In the absence of reinitialisation, incidents continue to be logged until there is memory overflow. Once this limit is reached, the oldest events are automatically flushed to make room for the most recent.

Detection of Decoupling Between Central Arterial Pressure and Peripheral Arterial Pressure The device described earlier can advantageously be complemented by a detection module of any possible decoupling between the peripheral arterial pressure (measured by radial artery catheter) and central or aortic arterial pressure. In fact, some particular clinical contexts (septic shock, or coming out of cardiopulmonary bypass) are characterized by major physiopathological modification of the characteristics of the peripheral arterial tree. This modification is likely to make measuring of the arterial pressure by radial artery catheter unworkable, which then no longer reflects central aortic arterial pressure. The latter controls organs as important as the heart, brain, etc.

Monitoring of the average level of central arterial pressure is therefore an important element of diagnosis, monitoring and goal-directed therapy, especially of those in a state of septic shock [14]. Also, the form and amplitude of peripheral arterial pressure used as input signal of continuous cardiac output measuring units allow evaluating the intravascular volume status under mechanical ventilation as well as that of other parameters (cardiac ventricular contractility, etc.) [3]. A detection module for decoupling between central and peripheral arterial pressures is therefore of particular interest in monitoring these clinical situations.

Figure 12A:
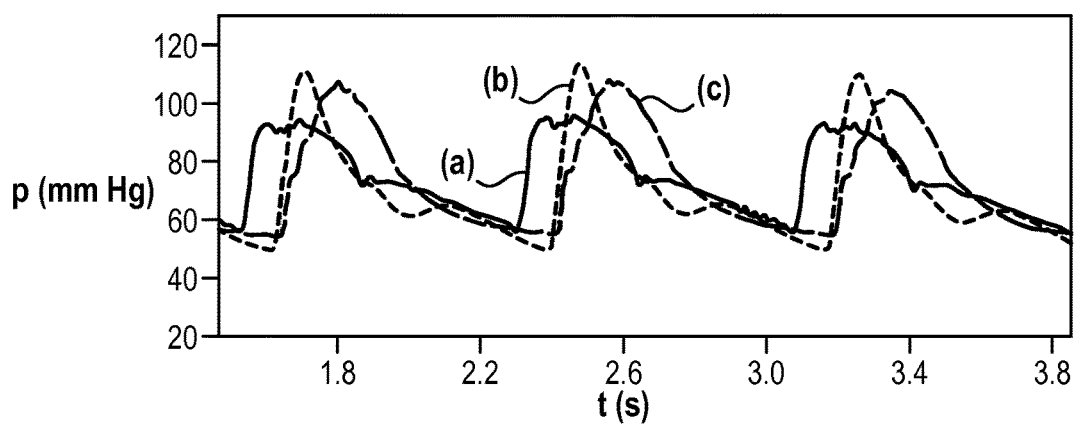
FIGS. 12A and 12B illustrate the variation in the aortic arterial pressure (curve (a)), radial arterial pressure (curve (b)) and femoral arterial pressure (curve (c)), respectively in a normal situation and in a septic shock situation.
Figure 12B:
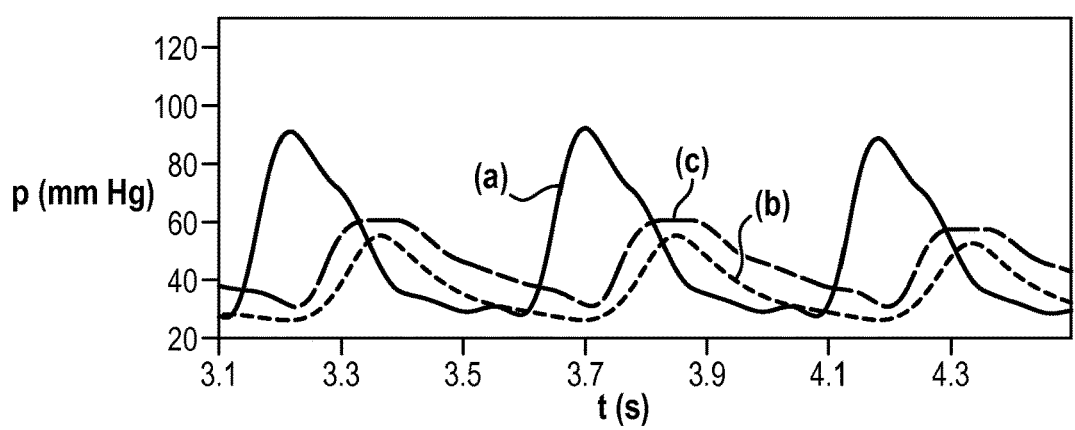

FIGS. 12A and 12B illustrate variation in aortic arterial pressure (curve (a)), radial (curve (b)) and femoral (curve (c)), respectively in a normal situation and in a septic shock situation [15]. In the normal state, radial arterial pressure has a systolic value greater than that of aortic pressure, especially because peripheral muscular conduit arteries are close to reflection sites. In a state of septic shock, this pressure gradient reverses.

It should be noted that this drop in systolic value in turn causes a moderate drop in the average level of peripheral radial arterial pressure relative to that of aortic pressure, this drop becoming clinically significant in some cases [14]. This modification can be explained by the following mechanism. A patient in septic shock retains central arterial compliance close to normal. However, he sees his peripheral arterial compliance increase due to the walls of the peripheral arteries being rich in vascular smooth-muscle cells, responsive to the nitric oxide pathway in septic shock and to modifications of the sympathetic tone.

These effects are far less important in the elastic central arteries, not very rich in vascular smooth-muscle cells. Detection of the decoupling can be done by two different methods, which can be complementary and are based on different principles of interpretation of pressure signals. Apart from the transducer 3 connected to the radial catheter by the for example 2, these methods employ applanation tonometry of brachial artery (in the elbow), or even applanation tonometry of carotid arteries.

Frequential Analysis

A first method is based on frequential analysis. The increase of peripheral arterial compliance causes repercussion on the frequency response of the peripheral arterial tree comparable to that of a low-pass filter which attenuates the high-frequency components. For the same input signal (aortic pressure), a different output signal (radial arterial pressure) is observed, depending on whether there is a normal situation or septic shock.

In the event of septic shock, the upper harmonics will be reduced relative to the lower harmonics. FIGS. 13A and 13B (from [15]) illustrate respectively aortic PAo and radial pressures P$_{radial}$ in a normal pig and in a pig in septic shock. In the normal event, conservation of the spectral content between aortic pressure and radial pressure is observed. However, in the case of septic shock, strong attenuation of the upper harmonics over radial arterial pressure (enclosed zone) is observed. The dotted line illustrates the effect of "low-pass" type mentioned earlier.

Continuous monitoring of the spectral content of the radial arterial pressure signal shows where needed evolution of this spectrum towards weakening of high harmonics. It is not possible to deduce therefrom that this comes obligatorily from an increase in peripheral arterial compliance. In fact, the cause can also be a change in the spectral content of the input signal (aortic pressure PAo).

To choose between these two interpretations, it is necessary to:

know the spectral content of the input signal (aortic pressure or brachial arterial pressure), measure the ratio RHAo=upper harmonics/lower harmonics of the input signal.

As aortic pressure is not accessible in current hospital practice, this measurement can be approached via brachial arterial pressure or even via carotid arterial pressure if the tonometry-measuring site of the latter is accessible. As this is a ratio of amplitudes, tonometry measuring of the brachial or carotid arterial pressure is sufficient.

compare the ratio RHao to the same ratio RHrad measured in radial artery.

A substantial difference (above a predetermined threshold) provides an indication of the decoupling between central arterial and peripheral pressure.

Measurement of the Progression Velocity of the Pulse Wave

A second method is based on the measurement of the progression velocity of the pulse wave. Some pathologies cause modifications of the tone of the walls of peripheral arteries, whereof the richness in vascular smooth-muscle cells via ratio to central arteries has already been emphasised.

In clinical septic shock situations or for patients coming out of cardiopulmonary bypass, the result is an increase in peripheral arterial compliance [15]. This increase in compliance of the peripheral arterial walls can be measured by the decrease in pulse wave velocity (PWV "Pulse Wave Velocity"). The parameters influencing this velocity are distributed between the changes in the elasticity of the arterial wall (incremental Young's modulus (Einc), the thickness of this wall (h), and the diameter of the radial artery (RAD), by using the Moens-Korteweg equation where p represents blood density:

$$PWV = \sqrt{\frac{Einc \cdot h}{\rho \cdot RAD}}$$

In the absence of an illustration in the literature of the decrease in pulse wave velocity in the field of septic shock, it is possible to find such in pharmacological studies and in coming out of cardiopulmonary bypass during cardiac surgery procedures. Therefore, Fok et al. observe a slowing of the pulse wave velocity when they inject vasodilatory substances such as donors of NO ("Nitric Oxide Donors") into the brachial artery upstream of the radial artery [16]. But septic shock causes release of this type of mediator. Therefore, Kanasawa et al show, in some of their patients coming out of cardiopulmonary bypass, that the amplitude and average level of arterial pressure drop progressively as the measuring site for arterial pressure moves away from the aorta towards the radial artery [17].

Figure 14:
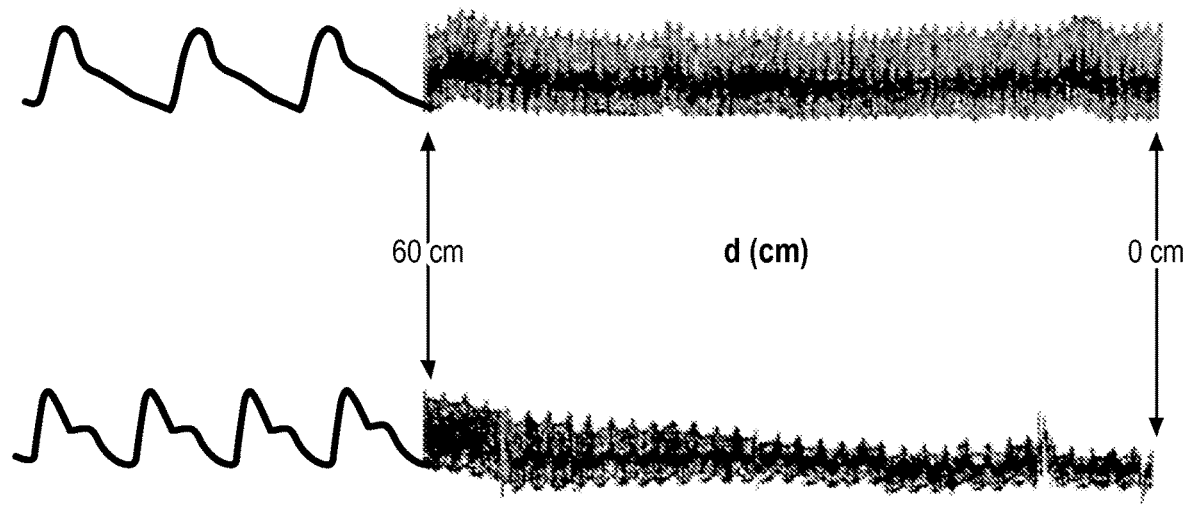
FIG. 14 illustrates respectively distribution of the arterial pressure of the aorta towards the radial artery in one of these patients before (curve from the top) and after (curve from the bottom) cardiopulmonary bypass, as a function of the relative distance to the radial artery.

FIG. 14 illustrates respectively the distribution of the arterial pressure of the aorta towards the radial artery in one of these patients before (curve from above) and after (curve from below) cardiopulmonary bypass, as a function of the distance d relative to the radial artery. This group of patients therefore presents a pressure gradient between the central arterial pressure and the peripheral arterial pressure. In this group of patients exhibiting a gradient between central arterial pressure and peripheral arterial pressure, the pulse wave velocity diminishes, as shown in FIG. 15.

Figure 15:
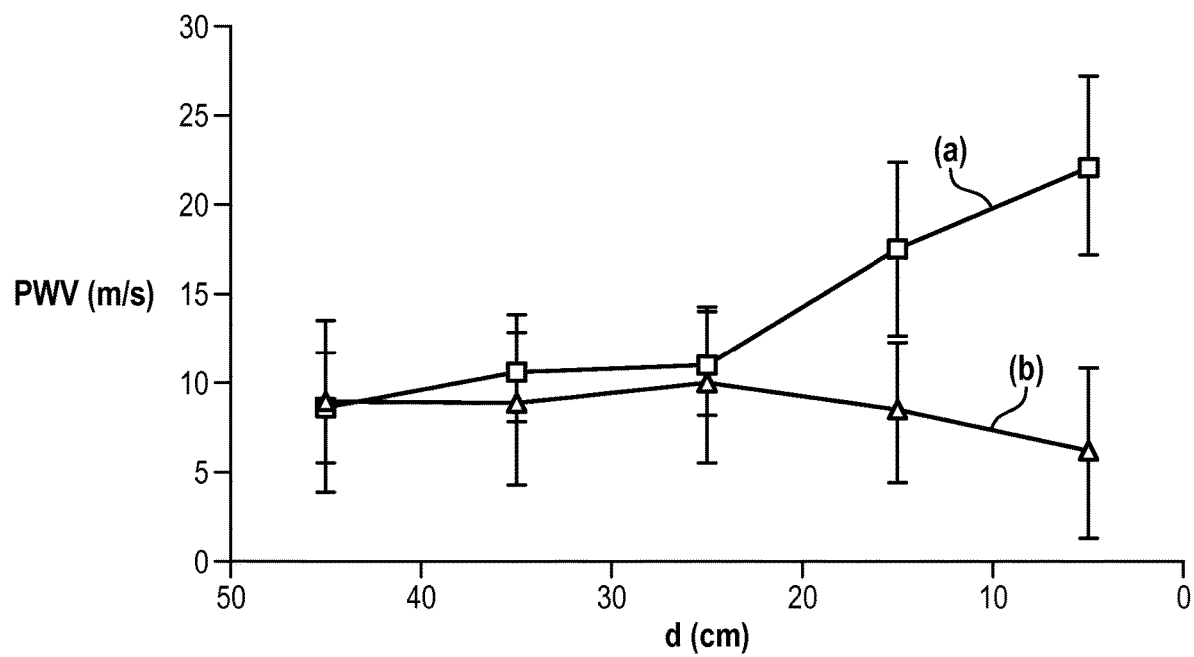
FIG. 15 illustrates the mean propagation velocity of the pulse wave as a function of the relative distance to the radial artery, before (curve (a)) and after (curve (b)) cardiopulmonary bypass in patients having an aortic to peripheral arterial pressure gradient.

FIG. 15 illustrates the mean pulse wave velocity as a function of the distance relative to the radial artery, before (curve (a)) and after (curve (b)) cardiopulmonary bypass in those patients mentioned hereinabove. The principle of the second detection method of decoupling consists of measuring the time delay separating the waveforms or the foot of these waveforms measured by tonometry of the brachial/ brachial artery on the one hand, and by radial artery catheter on the other hand. This time lets the monitoring device according to the invention, augmented by the decoupling detection option between central arterial and peripheral pressure estimate the current pulse wave velocity and compare it to normal known reference values. But it needs input by the operator of the brachial/radial distance by way of regulation incorporated into the tonometry device or the monitoring device itself.

A variant to this method uses two tonometric measurements: a brachial/brachial measurement and a carotid measurement. Because the impact of a decoupling situation on carotid/brachial propagation is generally less, while it is considerable over the brachial/radial propagation time, exploiting this imbalance provides an index for detection of decoupling. Another variant to this method can be used in case of inaccessibility of placement where carotid tonometry is applied to a patient hospitalised in intensive care (dressing, internal jugular vein access, etc.).

A transfer function calculates the aortic pressure from brachial artery tonometry [3]. One and/or the other of the decoupling detection methods is used by means of a tonometric casing which can be independent of the monitoring and correcting module. This casing typically comprises a transducer for measuring arterial pressure by tonometry, rechargeable battery feed, a display device and sealed buttons letting the operator interact with the device. This casing is a wireless or wired connection with the monitoring and correcting module.

Operation of this additional device is as follows. The monitoring and correction device fitted with this option permanently monitors radial arterial pressure via the hydraulic connection (basic functions described earlier). When the detection option for decoupling between central and peripheral pressures is in use, the device performs, also ongoing, an additional function which consists of monitoring the ratio RHrad (upper harmonics/lower harmonics) of the measured signal. If this ratio suddenly collapses, the device generates a specific warning.

The practitioner with the tonometric casing then measures tonometry of brachial and carotid arteries accompanied by input of the brachial/radial (and carotid/radial) distances. This input is done by way of touch and the display device incorporated into the tonometric casing.

If it is impossible to perform carotid tonometry (dressing, internal jugular vein access, etc.), the aortic pressure line is evaluated by a transfer function from the brachial pressure plotting [3]. The device uses methods of frequential analysis and pulse wave velocity analysis, as described previously. If the two methods detect no abnormal situation, the warning is cancelled. If the two methods supply diverging results, the practitioner is invited to repeat the tonometric measurements. If the two methods result in positive detection indicating a situation where measuring the arterial pressure catheter of the radial artery is no longer the reflection of the central pressure, the warning is transformed into an alarm. This data fusion device is original.

Finally, it is understood that the examples given above are only particular illustrations and in no way limiting as to the fields of application of the invention. Also, it is well known that the present invention does not at all relate to arterial cannulation of the patient, but only to a method and device for monitoring, once said catheter is introduced into the artery of the patient and is connected to the pressure transducer by the hydraulic connection, and where needed correcting the pressure-measuring signal provided by the transducer.

REFERENCES

[1] M. Cannesson, Arterial Pressure Variation and Goal-Directed Fluid Therapy. *J Cardiothorac Vasc Anesth.* 24 (3), 2010, pp. 487-497.
[2] J. Mayer, J. Boldt, R. Poland, A. Peterson and G. Manecke, Continuous Arterial Pressure Waveform-Based Cardiac Output Using the FloTrac/Vigileo: A Review and Meta-analysis. *J Cardiothorac Vasc Anesth.* 23 (3), 2009, pp. 401-406.
[3] R. Thiele, M E. Durieux, Arterial waveform analysis for the anesthesiologist: past, present, and future concepts. *Anesth Analg.* 113 (4), 2011, pp. 766-776.
[4] M. Gardner, Direct Blood Pressure Measurement—Dynamic Response Requirements, *Anesthesiology*, 54, 1981, pp. 227-236.
[5] C. Promonet, D. Anglade, A. Menaouar, S. Bayat, M. Durand, A. Eberhard and F. Grimbert, Time-dependent Pressure Distortion in a Catheter-Transducer System, *Anesthesiology*, 92 (1), 2000, pp. 208-218.
[6] M. Allan, W. Gray, J. Asbury, Measurement of Arterial Pressure Using Catheter-Transducer Systems, *Br J Anaesth*, 60, 1988, pp. 413-418.
[7] B. Kleinman, Understanding natural frequency and damping and how they relate to the measurement of blood pressure, *J Clin Monit,* 5 (2), 1989, pp. 137-147.
[8] E. Billiet and F. Colardyn, Pressure measurement evaluation and accuracy validation: the Gabarith test, *Int Care Med.* 24 (12), 1998, pp. 1323-1326.
[9] A. W. Paulsen, *Implications for clinical monitoring of intra-arterial blood pressure based on the frequency content of worst-case pressure waveforms, Medical Instrumentation & Technology*, May-June 1993, pp. 217-234.
[10] Patent DE 39 27 990, 28 Feb. 1991.
[11] R. Brower, W. Spaans, P. Rewiersma and G. Meester, A fully automatic device for compensating for artifacts in conventional catheter-manometer pressure recordings, *Biomed Eng,* 10, 1975, pp. 305-310.
[12] Y. Kinefuchi, T. Suzuki, M. Takiguchi, Y. Yamasaki and M. Yamamoto, Evaluation of dynamic response of catheter-manometer systems for pulmonary arterial pressure, *J Appl Physiol,* 77 (4), 1994, pp. 2023-2028.
[13] A. Ercole, Attenuation in invasive blood pressure measurement system, *Br J Anaesth.* 96 (5), 2006, pp. 560-562.
[14] Dellinger R P, Levy M M, Carlet J M, Bion J, Parker M M, Jaeschke R, Reinhart K, Angus D C, Brun-Buisson C, Beale R, Calandra T, Dhainaut J F, Gerlach H, Harvey M, Marini J J, Marshall J, Ranieri M, Ramsay G, Sevransky J, Thompson B T, Townsend S, Vender J S, Zimmerman J L, Vincent J L; International Surviving Sepsis Campaign Guidelines Committee; American Association of Critical-Care Nurses; American College of Chest Physicians; American College of Emergency Physicians; Canadian Critical Care Society; European Society of Clinical Microbiology and Infectious, Diseases; European Society of Intensive Care Medicine; European Respiratory, Society; International Sepsis Forum; Japanese Association for Acute Medicine; Japanese Society of Intensive Care Medicine; Society of Critical Care Medicine; Society of Hospital Medicine; Surgical Infection Society; World Federation of Societies of Intensive and Critical Care Medicine. Surviving Sepsis Campaign: international guidelines for management of severe sepsis and septic shock: 2008. *Crit Care Med.* 2008 January; 36(1):296-327. Erratum in: *Crit Care Med.* 2008 April; 36(4):1394-6.
[15] F. Hatib et al, Peripheral vascular decoupling in porcine endotoxic shock, J. Appl. Physiol. 111: 853-860.
[16] H. Fok et al, Regulation of Vascular Tone and Pulse Wave Velocity in Human Muscular Conduit Arteries—Selective Effects of Nitric Oxide Donors to Dilate Muscular Arteries Relative to Resistance Vessels, Hypertension, November 2012, pp. 1220-1225.
[17] M. Kanazawa, Relationship between Aortic-to-radial Arterial Pressure Gradient after Cardiopulmonary Bypass and Changes in Arterial Elasticity, Anesthesiology, V. 99, No. 1, July 2003.
[18] M. Shimada et al, Estimation of Aortic-to-radial Artery Distribution of Arterial Wall Elasticity, Tokai J. Exp. Clin. Med., Vol. 33, No. 1, pp 1-5, 2008.

The invention claimed is:

1. A continuous monitoring method for evaluating quality of an arterial pressure measurement made by a pressure transducer connected, by a hydraulic connection, to a catheter previously introduced into an artery of a patient, the hydraulic connection transmitting to the transducer an arterial pressure signal of the patient, called incident signal applied to an arterial inlet of the catheter and the transducer transforming the signal transmitted by the hydraulic connection into an electric signal, called measured signal, the method comprising:
    determining, from the measured signal, dynamic parameters of the hydraulic connection, the parameters comprising a natural frequency and a damping coefficient of the hydraulic connection,
    analyzing the frequential content of the incident signal so as to determine the maximal frequency component of the signal, detecting, from at least the dynamic parameters of the hydraulic connection, each one of the following three situations when or if it occurs:
- (a) an aptitude of the hydraulic connection to transmit the incident signal to the transducer with distortion lower than a threshold;
- (b) an aptitude of the hydraulic connection to transmit the incident signal to the transducer with distortion greater than the threshold and a possibility of correcting the measured signal;
- (c) an inaptitude of the hydraulic connection to transmit the incident signal to the transducer with distortion lower than the threshold and an impossibility of correcting the measured signal;

displaying visual information indicative of each one of the situations (a), (b) or (c) when or if it occurs, the visual information being different for each situation; and the method also comprising periodically applying first and second mechanical actions on an outer wall of tubing which forms the hydraulic connection and updating the dynamic parameters of the hydraulic connection based on a measured signal resulting from the first and second mechanical actions, wherein the first mechanical action comprises percussion of the outer wall of the tubing which forms the hydraulic connection and the natural frequency of the hydraulic connection is determined from an analysis of a measured signal in response to the first mechanical action; and the second mechanical action comprises a series of sinusoidal stresses of variable frequency applied to the outer wall of the tubing which forms the hydraulic connection and the damping coefficient of the hydraulic connection is determined from an analysis of a measured signal in response to the second mechanical action.

2. The method of claim 1, wherein at least one of the first and the second mechanical action is synchronised with a diastole or segmented and synchronised with several successive diastoles.

3. The method of claim 1, wherein determining the dynamic parameters of the hydraulic connection is done from at least one of
- analysis of a measured signal in response to at least one of; a fast flush and said mechanical action applied to the outer wall of the tubing which forms the hydraulic connection, and from
- analysis of the frequential content of the signal.

4. The method of claim 1, wherein the detecting one of the situations (a) or (c) comprises positioning, on a natural frequency-damping factor summary table, of a representative point of the dynamic parameters of the hydraulic connection relative to an area of tolerance determined by the maximal frequency component of the signal used.

5. The method of claim 1, further comprising, in the situation (b), correcting the measured signal as a function of the dynamic parameters of the hydraulic connection.

6. The method of claim 1, further comprising, in the situation (c), emitting of an alert signal.

7. The method of claim 6, wherein the alert signal comprises an indication of an action to be taken by clinical staff, such as a fast flush or replacement of the hydraulic connection and/or of the catheter.

8. The method of claim 1, further comprising recording the measured signal.

9. The method of claim 1, further comprising transmitting the measured signal to a processing system.

10. The method of claim 1, wherein the analysing the frequential content of the incident signal comprises detecting spectral slipping and/or variation in a relative weight of components of upper frequencies, and triggering an update of the dynamic parameters of the hydraulic connection based on the detection of spectral slipping and/or variation in a relative weight of components of upper frequencies of the incident signal.

11. The method of claim 1, further comprising detection of decoupling between a central arterial pressure and a radial arterial pressure of the patient, the detection comprising monitoring of the ratio between upper harmonics and lower harmonics of the measured radial arterial pressure signal and, if the ratio drops suddenly:
- generating an alert;
- requesting medical staff to perform applanation tonometry of brachial and/or carotid arteries;
- determining a ratio between the upper harmonics and the lower harmonics of the brachial and/or carotid pressure signal;
- comparing the ratio between the upper harmonics and the lower harmonics of the brachial and/or carotid pressure signal with a ratio between the upper harmonics and the lower harmonics of the radial arterial pressure measured signal;
- if a difference between the compared ratios is greater than a threshold, providing an indication of the decoupling.

12. The method of claim 11, wherein in case of impossibility to perform carotid applanation tonometry, aortic pressure is evaluated by a transfer function from a measurement of a brachial pressure.

13. The method of claim 1, further comprising detection of decoupling between a central arterial pressure and a radial arterial pressure of the patient, the detection comprising performing applanation tonometry of the brachial/brachial and/or carotid artery, monitoring of a propagation velocity of a pulse wave of the patient determined from the applanation tonometry and the measured radial arterial pressure signal, and comparison of the velocity with a reference value.

14. The method of claim 13, further comprising detection of decoupling between a central arterial pressure and a radial arterial pressure of the patient, the detection comprising monitoring of the ratio between upper harmonics and lower harmonics of the measured radial arterial pressure signal and, if the ratio drops suddenly:
- performing applanation tonometry of brachial and/or carotid arteries;
- determining a ratio between the upper harmonics and the lower harmonics of the brachial and/or carotid pressure signal;
- comparison of the ratio between the upper harmonics and the lower harmonics of the brachial and/or carotid pressure signal with a ratio between the upper harmonics and the lower harmonics of the measured radial arterial pressure signal,
- wherein each of the detection steps of decoupling is performed and in that, if each of the detections reveals decoupling of the central arterial pressure and radial arterial pressure of the patient, an alarm is issued.

15. A continuous monitoring device for evaluating quality of the blood arterial pressure measurement done by:
(i) a system comprising:
a pressure transducer connected, by a hydraulic connection, to a catheter introduced into an artery of a patient, the hydraulic connection transmitting to the transducer an arterial pressure signal of the patient, applied to an arterial inlet of the catheter, and the transducer transforming the signal transmitted by the hydraulic connection into an electric signal;

(ii) the continuous monitoring device further comprising:

a casing configured to be plugged between the pressure transducer and a monitor displaying the measured signal, a processor enclosed in the casing, the processor being configured to:
  determine, from a measured signal, dynamic parameters of a hydraulic connection, the parameters comprising a natural frequency and the damping coefficient of the hydraulic connection,
  analyze the frequential content of an incident signal so as to determine a maximal frequency component of the signal to be transmitted,
  detect, from at least the dynamic parameters of the hydraulic connection, each one of the following three situations when or if it occurs:
    (a) an aptitude of the hydraulic connection to transmit the incident signal to the transducer with distortion lower than a threshold;
    (b) an aptitude of the hydraulic connection to transmit the incident signal to the transducer with distortion greater than the threshold and the aptitude of the processor to correct the measured signal;
    (c) an inaptitude of the hydraulic connection to transmit the incident signal to the transducer with distortion lower than the threshold and the inaptitude of the processor to correct the measured signal;

a user interface configured to display a visual information indicative of each one of the situations (a), (b) or (c) when or if it occurs, the visual information being different for each situation; and an actuator enclosed in the casing, the actuator being adapted to periodically apply first and second mechanicals action to the outer wall of the tubing which forms the hydraulic connection, wherein the actuator is configured to apply the first mechanical action as a percussion of the outer wall of the tubing which forms the hydraulic connection, and the processor determines the natural frequency of the hydraulic connection by analyzing a measured signal in response to the first mechanical action; and the actuator is further configured to apply the second mechanical action as a series of sinusoidal stresses of variable frequency applied to the outer wall of the tubing which forms the hydraulic connection, and the processor determines the damping coefficient of the hydraulic connection by analyzing a measured signal in response to the second mechanical action.

16. The device of claim 15, wherein characterized in that the processor comprises:
  a first processor adapted to determine the dynamic parameters of the hydraulic connection, analyse the frequential content of the incident signal, detect one of the situations (a), (b) or (c) and, in the situation (b), define correction parameters of the measured signal as a function of the dynamic parameters of the hydraulic connection; and
  a second processor adapted to continuously correct the measured signal from the correction parameters defined by the first processor in the situation (b) to generate the corrected signal.

17. The device of claim 16, wherein the first and second processors are connected so as to ensure redundant treatments.

18. The device of claim 15, wherein the actuator comprises a piezoelectric actuator or an electromechanical device.

19. The device of claim 15, further comprising a wired connection between the processor and the actuator, the wired connection being adapted to supply the actuator with at least one of: a synchronisation signal with a diastole and electric power coming from the processor.

20. The device of claim 19, wherein the actuator comprises a rechargeable battery.

21. The device of claim 15, further comprising a wireless connection between the processor and the actuator, the wireless connection being adapted to supply the actuator with a synchronisation signal with a diastole emitted by the processor.

22. The device of claim 15, wherein the actuator is adapted to be attached to the hydraulic connection at a distance from the processor.

23. The device of claim 15, further comprising a processing system adapted to communicate with the processor.

24. The device of claim 23, wherein the processing system is adapted to process the measured signal transmitted by the processor.

25. The device of claim 23, wherein the processing system is also adapted to transmit to the processor instructions for modifying the operation of the processor.

26. The device of claim 23, wherein said processing system is included in a personal digital assistant.

27. The device of claim 15, further comprising a casing of applanation tonometry.

28. A continuous monitoring method comprising:
  evaluating quality of an arterial pressure measurement made by a pressure transducer connected to a catheter via a hydraulic connection which transmits to the transducer an incident signal applied to an arterial inlet of the catheter and the transducer transforming the signal transmitted by the hydraulic connection into a measured signal, the evaluating comprising:
    (a) determining, from the measured signal, dynamic parameters of the hydraulic connection, the parameters comprising a natural frequency and a damping coefficient of the hydraulic connection, and the hydraulic connection being modelled by a second order physical system;
    (b) analyzing the frequential content of the incident signal so as to determine a maximal frequency component;
    (c) detecting, from at least the dynamic parameters of the hydraulic connection, each of the following possible situations:
      (i) an aptitude of the hydraulic connection to transmit the incident signal to the transducer with distortion lower than a threshold;
      (ii) an aptitude of the hydraulic connection to transmit the incident signal to the transducer with distortion greater than the threshold;
      (iii) an inaptitude of the hydraulic connection to transmit the incident signal to the transducer with distortion lower than the threshold;
    (d) displaying visual information indicative of each one of the situations (i), (ii) or (iii) when or if it occurs, the visual information being different for each situation;
    (e) periodically applying first and second mechanical actions on an outer wall of tubing which forms the hydraulic connection and updating the dynamic parameters of the hydraulic connection based on a measured signal resulting from the first and second mechanical actions;

(f) the first mechanical action comprising percussion of the outer wall of the tubing, and the natural frequency of the hydraulic connection is determined from an analysis of the measured signal in response to the first mechanical action; and (g) the second mechanical action comprising a series of sinusoidal stresses of variable frequency applied to the outer wall of the tubing, and the damping coefficient of the hydraulic connection is determined from an analysis of the measured signal in response to the second mechanical action.

29. The method of claim 28, wherein the second order physical system has a transfer function H(p) defined by the following formula:

$$H(p) = \frac{1}{\frac{p^2}{\omega_0^2} + \frac{2z}{\omega_0}p + 1}$$

where
p is a Laplace variable,
z is the damping factor and
$\omega_0$ is a natural pulsation, expressed in rad/s and equal to $2\pi f_0$, where $f_0$ is the natural frequency, expressed in Hz.

* * * * *